(12) United States Patent
Lo et al.

(10) Patent No.: US 12,167,918 B2
(45) Date of Patent: Dec. 17, 2024

(54) METHOD AND SYSTEM FOR TARGETED AND ADAPTIVE TRANSCUTANEOUS SPINAL CORD STIMULATION

(71) Applicant: NICHE BIOMEDICAL, INC., Los Angeles, CA (US)

(72) Inventors: Yi-Kai Lo, Los Angeles, CA (US); Rachel Yung, Los Angeles, CA (US); Po-Min Wang, Los Angeles, CA (US); Alexander Barnes Baldwin, Los Angeles, CA (US); Chia-Hung Ni, Los Angeles, CA (US)

(73) Assignee: NICHE BIOMEDICAL, INC., Los Angeles, CA (US)

( * ) Notice: Subject to any disclaimer, the term of this patent is extended or adjusted under 35 U.S.C. 154(b) by 273 days.

(21) Appl. No.: 17/762,800

(22) PCT Filed: Sep. 28, 2020

(86) PCT No.: PCT/US2020/052992
§ 371 (c)(1),
(2) Date: Mar. 23, 2022

(87) PCT Pub. No.: WO2021/062345
PCT Pub. Date: Apr. 1, 2021

(65) Prior Publication Data
US 2022/0386935 A1    Dec. 8, 2022

Related U.S. Application Data

(60) Provisional application No. 62/907,475, filed on Sep. 27, 2019.

(51) Int. Cl.
*A61B 5/389* (2021.01)
*A61B 5/00* (2006.01)
(Continued)

(52) U.S. Cl.
CPC ............ *A61B 5/389* (2021.01); *A61B 5/0075* (2013.01); *A61B 5/1116* (2013.01);
(Continued)

(58) Field of Classification Search
None
See application file for complete search history.

(56) References Cited

U.S. PATENT DOCUMENTS 6,456,885 B1 *   9/2002   Shiba ................. A61N 1/36003
                                                            607/48
8,165,685 B1 *   4/2012   Knutson ............ A61N 1/36034
                                                            607/2

(Continued)

FOREIGN PATENT DOCUMENTS

KR    10-2012-0135219 A    12/2012
KR    10-2016-0008162 A    1/2016
(Continued)

OTHER PUBLICATIONS

1st Office Action in Primary examination for corresponding Taiwan patent Application No. 109133685, Applicant Niche Biomedical, Inc., pp. 1-8.
(Continued)

*Primary Examiner* — Carl H Layno
*Assistant Examiner* — Manolis Pahakis
(74) *Attorney, Agent, or Firm* — Tarolli, Sundheim, Covell & Tummino LLP

(57) ABSTRACT

A transcutaneous electrical stimulation system is provided that can include a number of features. In one implementation, the system can include a plurality of electrodes configured to be in contact with a skin surface of a patient. The system can further include a flexible hub electrically connected to the electrodes and configured to be in contact with the patient. A bend sensor can be disposed in the hub and
(Continued)

configured to measure a curvature of the hub. The system can include a signal processing device electrically coupled to the plurality of electrodes and the bend sensor, the signal processing device being configured to change stimulation settings of the plurality of electrodes based on the curvature of the hub. In some implementations, the system can include a multi-channel stimulator. Methods of use are also provided.

16 Claims, 21 Drawing Sheets

(51) Int. Cl.
| | |
|---|---|
| *A61B 5/01* | (2006.01) |
| *A61B 5/021* | (2006.01) |
| *A61B 5/024* | (2006.01) |
| *A61B 5/11* | (2006.01) |
| *A61B 5/145* | (2006.01) |
| *A61N 1/04* | (2006.01) |
| *A61N 1/36* | (2006.01) |

(52) U.S. Cl.
CPC ....... *A61N 1/0456* (2013.01); *A61N 1/36014* (2013.01); *A61N 1/36031* (2017.08); *A61B 5/01* (2013.01); *A61B 5/021* (2013.01); *A61B 5/024* (2013.01); *A61B 5/14517* (2013.01)

(56) References Cited

U.S. PATENT DOCUMENTS

| | | | |
|---|---|---|---|
| 9,314,190 B1* | 4/2016 | Giuffrida | A61N 1/36003 |
| 2007/0162087 A1 | 7/2007 | Wahlstrand et al. | |
| 2008/0009782 A1 | 1/2008 | Gale et al. | |
| 2008/0027507 A1 | 1/2008 | Bijelic et al. | |
| 2008/0288020 A1* | 11/2008 | Einav | A61N 1/36003 |
| | | | 607/48 |
| 2011/0319975 A1 | 12/2011 | Ho et al. | |
| 2012/0310303 A1* | 12/2012 | Popovic | A61N 1/0492 |
| | | | 607/48 |
| 2013/0030277 A1* | 1/2013 | Fahey | A61N 1/0452 |
| | | | 607/48 |
| 2013/0041235 A1 | 2/2013 | Rogers | |
| 2013/0090541 A1 | 4/2013 | MacFarlane et al. | |
| 2014/0336722 A1* | 11/2014 | Rocon De Lima | |
| | | | A61N 1/36139 |
| | | | 607/45 |
| 2014/0358193 A1* | 12/2014 | Lyons | A61N 1/37229 |
| | | | 607/48 |
| 2015/0306373 A1* | 10/2015 | Bouton | A61N 1/0456 |
| | | | 607/148 |
| 2016/0121109 A1* | 5/2016 | Edgerton | A61N 1/06 |
| | | | 607/45 |
| 2016/0144172 A1* | 5/2016 | Hsueh | A61B 5/389 |
| | | | 607/48 |
| 2017/0087362 A1* | 3/2017 | Papp | A61N 1/3787 |
| 2017/0224985 A1* | 8/2017 | Debur | A61N 1/0452 |
| 2018/0154140 A1* | 6/2018 | Bouton | A61B 5/293 |
| 2018/0169400 A1* | 6/2018 | Wong | A61N 1/0484 |
| 2018/0236217 A1* | 8/2018 | Hamner | A61N 1/048 |
| 2018/0289955 A1 | 10/2018 | Southwell | |
| 2018/0326205 A1* | 11/2018 | Cheng | A61N 1/36021 |
| 2019/0022371 A1* | 1/2019 | Chang | A61N 1/36 |
| 2019/0083784 A1* | 3/2019 | Raghunathan | A61N 1/36057 |
| 2020/0061378 A1* | 2/2020 | Ganguly | A61B 5/374 |
| 2020/0093400 A1* | 3/2020 | Hamner | A61B 5/389 |
| 2020/0139116 A1* | 5/2020 | Samejima | A61N 1/36003 |
| 2020/0147383 A1* | 5/2020 | Caban | A61N 1/36031 |
| 2020/0254260 A1* | 8/2020 | Bakker | A61N 1/36167 |
| 2020/0306528 A1* | 10/2020 | Linden | A61N 1/36114 |
| 2020/0391027 A1* | 12/2020 | Thakkar | A61N 1/0452 |

FOREIGN PATENT DOCUMENTS

| | | |
|---|---|---|
| TW | M425675 U | 4/2012 |
| TW | 201632223 A | 9/2016 |
| TW | 201703810 A | 2/2017 |
| TW | 201831137 A | 9/2018 |
| WO | 2018/106843 A1 | 6/2018 |

OTHER PUBLICATIONS

EP Search Report for corresponding Application No. 109133685, dated Sep. 27, 2019, 1 page.
Translation of First Office Action for corresponding Taiwan patent Application No. 109133685, date of completion of search Dec. 16, 2023, pp. 1-12.
Matthias Krenn et al.: "Multi-Electrode Array for Transcutaneous Lumbar Posterior Root Stimulation" , Artificial Organs, Blackwell Scientific Publications, Inc., Boston, US, vol. 39, No. 10, Oct. 16, 2015 (Oct. 16, 2015), pp. 834-840, XP071484820, Issn: 0160-564X, DOI: 10.1111/AOR.12616.
The European Search Report regarding corresponding Application No. 20869182.4-1126/4041377 PCT/US2020052992 with a mailing date of Sep. 13, 2023, pp. 1-9.
Office Action for Korean Patent Application No. 10-2022-7013622, titled Method and System for Targeted and Adaptive Transcutaneous Spinal Cord Stimulation with a filing date of Apr. 22, 2022; Korean Intellectual Property Office Notice Requesting Submission of Opinion for Applicant Niche Biomedical, Inc., with a delivery date of Mar. 25, 2024, 11 pages.
Office Action for IL Patent Application No. 308981, dated Mar. 17, 2024, 5 pages.
PCT International Search Report for corresponding International Application Serial No. PCT/US2020/052992, mailed Mar. 2, 2021, pp. 1-19.
Office Action for Patent Application No. 20 869 182.4-1122, dated Jul. 3, 2024, 6 pages.
Search report dated Sep. 27, 2019 for corresponding TW application No. 113108932, 1 page.
1st Office Action issued for TW corresponding application No. 113108932, 5 pages.

* cited by examiner

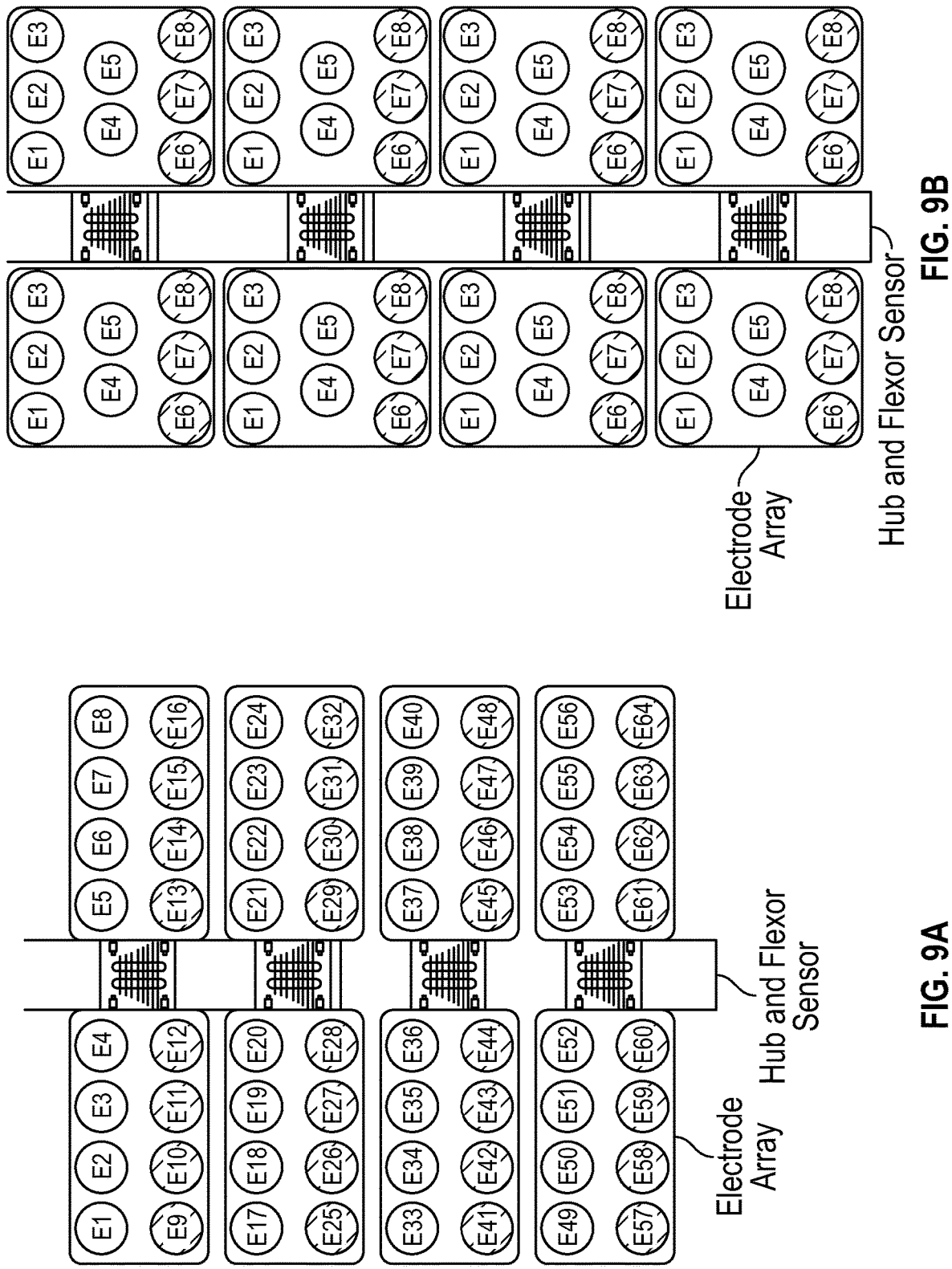

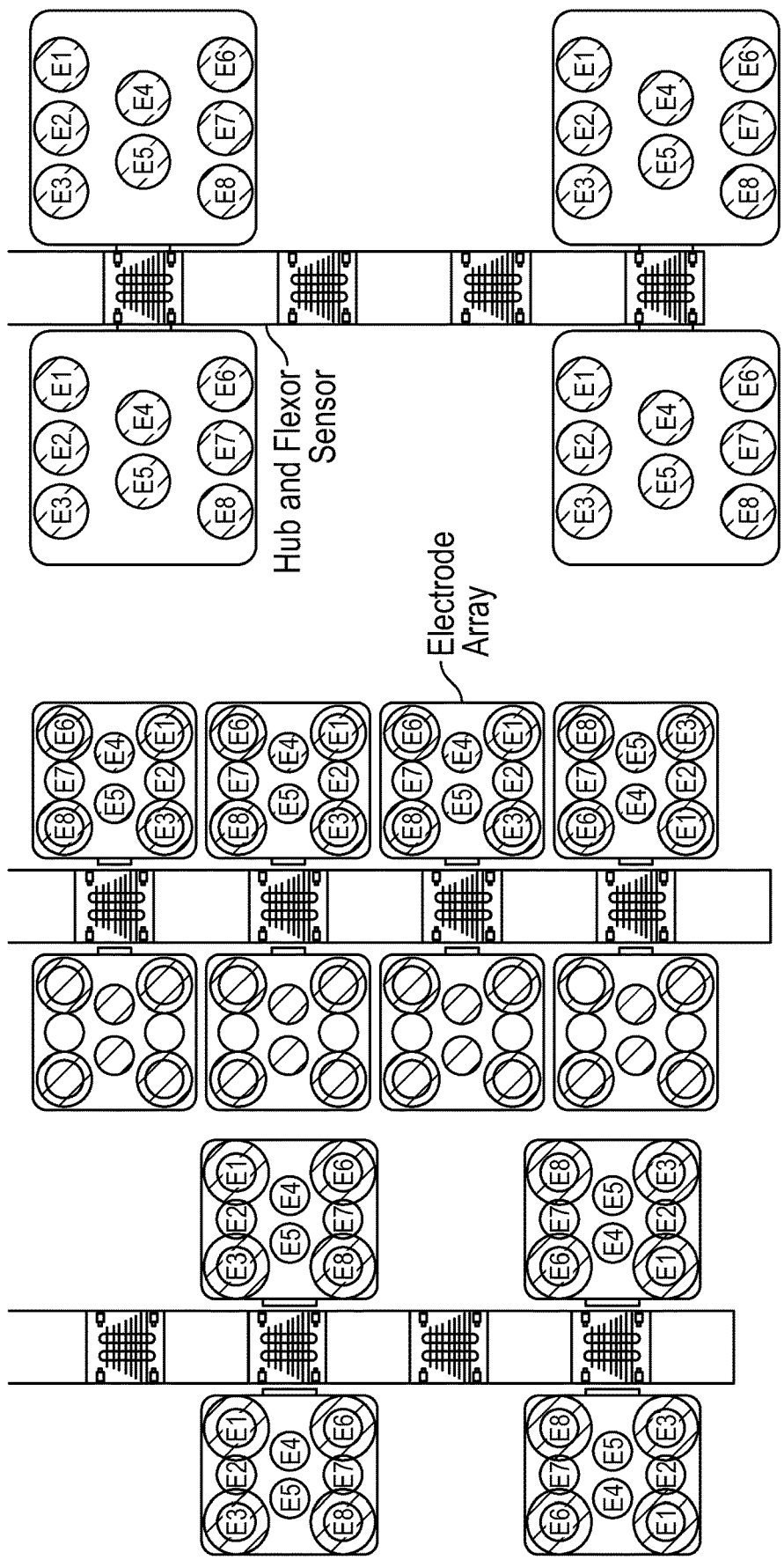

METHOD AND SYSTEM FOR TARGETED AND ADAPTIVE TRANSCUTANEOUS SPINAL CORD STIMULATION

CROSS REFERENCE TO RELATED APPLICATIONS

This application is a National Stage Entry of International Application Number PCT/US2020/052992, filed Sep. 28, 2020, which claims the benefit of U.S. Provisional Application No. 62/907,475, filed Sep. 27, 2019. The contents of these applications are incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

The spinal nervous system is a complex part in humans that transmits signals between the brain and the rest of the body, including internal organs. These signals are instrumental in the control and coordination of actions and sensory information in the body. A proper understanding of the spinal nervous system anatomy can inform and influence related medical interventions.

The human spinal cord has 31 nerve segments in total. The first 8 cervical segments form 8 pairs of cervical nerves. The nerves originating from the anterior, i.e., front part of the five cervical segments, C1 to C5, form the cervical plexus. C5 to C8 are responsible for the coordination of arm, shoulder and hand nerves. Out of the next twelve thoracic nerves, the first one, T1 also supports the arm, shoulder and hand nerves. The network of nerves originating from C5 to T1 is called the brachial plexus and this network handles the entire motor and sensory function of the hand and arm. In order for the human torso to function properly, various segments of the spinal cord work together to innervate muscles in the neck, chest, back, and abdomen area.

The topological organization of each spinal segment is described in the following: The cervical plexus supplies sensory support to the neck area and some motor support as well, especially to the diaphragm. Lesser Occipital originates from the $2^{nd}$ cervical spine (C2) and is a sensory nerve connecting to some parts of the ear, the skin behind the ears, posterolateral neck; Great Auricular nerve originates from the $2^{nd}$ and $3^{rd}$ spines (C2 and C3) and is a sensory nerve connecting to most of the ear, mastoid region behind the ear, and the region around the jawbone; Transverse Cervical Nerve originates from C3 and is a sensory nerve connecting to Anterior and lateral neck, underside of chin; Ansa Cervicalis nerve originates from C1, C2, and C3 spinal segments and controls the movement of the neck and head; Supraclavicular nerve originates from C3 and C4 spinal segments and is a sensory nerve connecting to the lower anterior and lateral neck, shoulder anterior chest; Phrenic nerve contains both sensor and motor nerves and supplies the major motor function to diaphragm and is instrumental in breathing. Brachial plexus handles the entire motor and sensory function of the hand and arm and innervates with C5 to Thoracic 1 (T1). The musculocutaneous nerve innervates the muscles in the anterior, i.e., front portion of the arm. These nerves help flex the muscles in the upper arm at the shoulder and elbow. These nerves receive sensory information from both the front and back part of the forearm. Musculocutaneous nerves are instrumental for humans to supinate (turn/rotate) their arm and controls Brachialis, biceps brachii, coracobrachialis muscles. The axillary nerve carries nerve fibers from the region around the armpits and to the triceps area in the back of the forearm. This nerve supplies three muscles—deltoid, triceps and teres minor, which is one of the rotator cuff muscle. It carries sensory information from the shoulder joint, as well as the skin covering the region below the deltoid muscle. The radial nerve supplies the muscles in the posterior, i.e., the back portion of the entire arm (Triceps brachii, brachioradialis, anconeus, extensor muscles of the posterior arm and forearm). It also provides sensory support to most of the lateral aspect of the posterior forearm including the wrist. The median nerve runs down the full length of the arm into the hand. The median nerve innervates the anterior, i.e., the front of the entire forearm (Forearm flexors, thenar eminence, lumbricals of the hand 1-2). It supplies to the muscles of the front of the forearm and muscles on the palm directly under the thumb. It is responsible for controlling the coarse movements of the hand. It receives sensory information from the majority of the lateral portion of the hand as well as the tips of the thumb and three fingers. The ulnar nerve controls the fine movements of the fingers, as well as the muscles in the forearm. It receives sensory information from the medial, i.e., middle portion of the palm, the medial portion of the fourth finger, and the entire little finger. It also provides sensory innervation to the dorsal medial hand, i.e., the middle portion of the back of the hand (Hypothenar eminence, some forearm flexors, thumb adductor, lumbricals 3-4, interosseous muscles).

The nerves branching from the spinal cord segment T1-T12 are called thoracic nerves. The first eleven thoracic nerves are situated between the ribs and are therefore termed intercostal. T12 lies below the last rib. T1-T12, along with some nerves of the brachial plexus that support the shoulder as well as the cervical plexus, control the functioning of the torso. The first six thoracic nerves are responsible for the motor function of intercostal muscles and trunk above the waist. The lateral branches of some of the upper thoracic nerves also give sensory supply to the skin; these nerves supply the rectus abdominis.

The nerves from the anterior section of spinal cord segment L1-L4 form the lumbar plexus. The lumbar plexus supplies muscles in the lower back and abdomen, including 1) Iliohypogastric nerve that originates from T12 and L1 spinal segment takes sensory input from skin of lower anterior abdominal and posterolateral gluteal regions, and exert motor control on internal and external abdominal oblique and transverse abdominal muscles; Ilioinguinal nerve that originates from the L1 spinal segment takes sensory input from the skin of upper medial thigh, male scrotum and female labia, and exerts motor control on internal abdominal oblique; Genitofemoral nerve that originates from L1 and L2 segment takes the sensory input from the skin of middle anterior thigh, male scrotum, and female labia majora, and exert control on male cremaster muscle; Lateral Femoral Cutaneous nerve that originates from L2 and L3 spinal segments and takes sensory input from the skin of anterior and upper lateral thigh; Femoral nerve that originates from L2 to L4 spines takes sensory input from the skin of anterior, medial and lateral thigh and knee; skin of medial leg and foot; hip and knee joints and exerts control on Iliacus pectineus, quadriceps femoris, and sartorius muscles; Obturator nerve that originates from L2, L3 and L4 spine, takes sensory input from the skin of medial thigh, hip and knee joints, and exerts motor control on obturator externus and medial thigh muscles. As the spinal nervous system anatomy is well defined, it can be applied to identify and correlate the treatment of medical conditions for injuries or diseases of the nervous system.

Spinal cord stimulation is an established and accepted clinical treatment for patients with certain chronic diseases or impairments related to the central and/or peripheral nervous system. The standard spinal cord stimulation device includes an implanted electrode array, an implantable pulse generator, and lead wires. During surgical implantation, the electrodes are placed on the epidural spinal cord or spinal ganglion roots and are connected via lead wires to the implantable pulse generator. The implantable pulse generator is programmed to send electrical stimulation signals to the electrodes in order to stimulate the spinal cord. Numerous such stimulation systems exist.

One problem with implantable spinal cord stimulator systems are that the electrodes must be implanted within close proximity to vital neurological structures. Though this provides high stimulation selectivity, patients also must be eligible for and undergo a surgical procedure, which introduces additional risks of infection, hematoma, damage to critical neural structures, leakage of cerebral spinal fluid, and other complications related to the procedure or related to pre-existing comorbidities. Furthermore, any foreign object implanted in the human body requires constant monitoring and maintenance and migration of the electrode position causes further encumbrance to the patients as they need to re-calibrate/re-program stimulation settings to maintain the treatment effectiveness.

An alternative to spinal implants is transcutaneous spinal cord stimulation, where removable electrodes are placed on the surface of the skin. Transcutaneous spinal cord stimulation is emerging as an innovative neuromodulation therapy with multiple clinical applications, including motor function rehabilitation in spinal cord injury (SCI) and stroke, traumatic brain injury, muscle spasticity modification, multiple sclerosis, essential tremor, chronic refractory pain treatment (back, visceral, cancer), autonomic function rehabilitation, gastrointestinal (GI) function rehabilitation, immunology, urinary function, and blood/bone marrow regeneration. Neuromodulation provides access to remaining/surviving neural circuitries and pathways to ameliorate and treat the above disease, injuries, and deficits. About one to five electrodes can be used at one time, and they are connected via wires to an external stimulator, which applies stimulation at desired settings. However, conventional transcutaneous stimulator systems suffer from very poor stimulation selectivity and their claimed stimulation selectivity is done by merely placing the electrode on the skin close to the underlying biologic target. Due to the sophisticated inhomogeneity of human anatomy, the above approach results in high electric fields off-target and limits stimulation of the desired spinal segment.

In particular, for the motor impairment due to SCI, the supraspinal-spinal connectivity is disrupted, resulting in paralysis and dysfunction of multiple physiological systems. Clinical researches using epidural spinal stimulation has been shown beneficial to help SCI patients regain motor and improve autonomic functions. Other electrophysiological and computational studies also demonstrated that it is the afferent neurons that are directly and electrically stimulated by epidural or transcutaneous stimulation and then interneurons residing in the spinal cord circuitries are triggered to activate motor neurons. While transcutaneous stimulation promises to modulate a broader range of spinal network to turn the spinal circuitries into a physiological state that can enable the voluntary control from the supraspinal command or enable the proprietary sensory inputs, conventional implementations continue to fall short by lacking stimulation focus. Still further, existing transcutaneous stimulation systems are limited by 1) the poor modularity of electrodes, including the quantity, size, and spacing, 2) the basic options for stimulation waveforms, 3) the lack of selectively stimulation (i.e., poor spatial stimulation resolution), 4) the lack of precisely timed or as-needed stimulation (i.e., prior arts mainly support tonic (continuous) stimulation that might affect the desired proprioceptive sensory input, 5) the time consuming calibration method, 5) the lack of automation based on real time biometric feedback, 6) the lack of portability, and 7) the stability and longevity of the electrode for daily use.

As the above shortcoming makes clear, the need remains for a transcutaneous stimulation system suited to supporting the above needed features and limitation on current technologies.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 8, 9A-9B, 10A-10D, and 11A-11C shows various configurations of a flexible hub and electrode arrays.

SUMMARY

Figure 1:
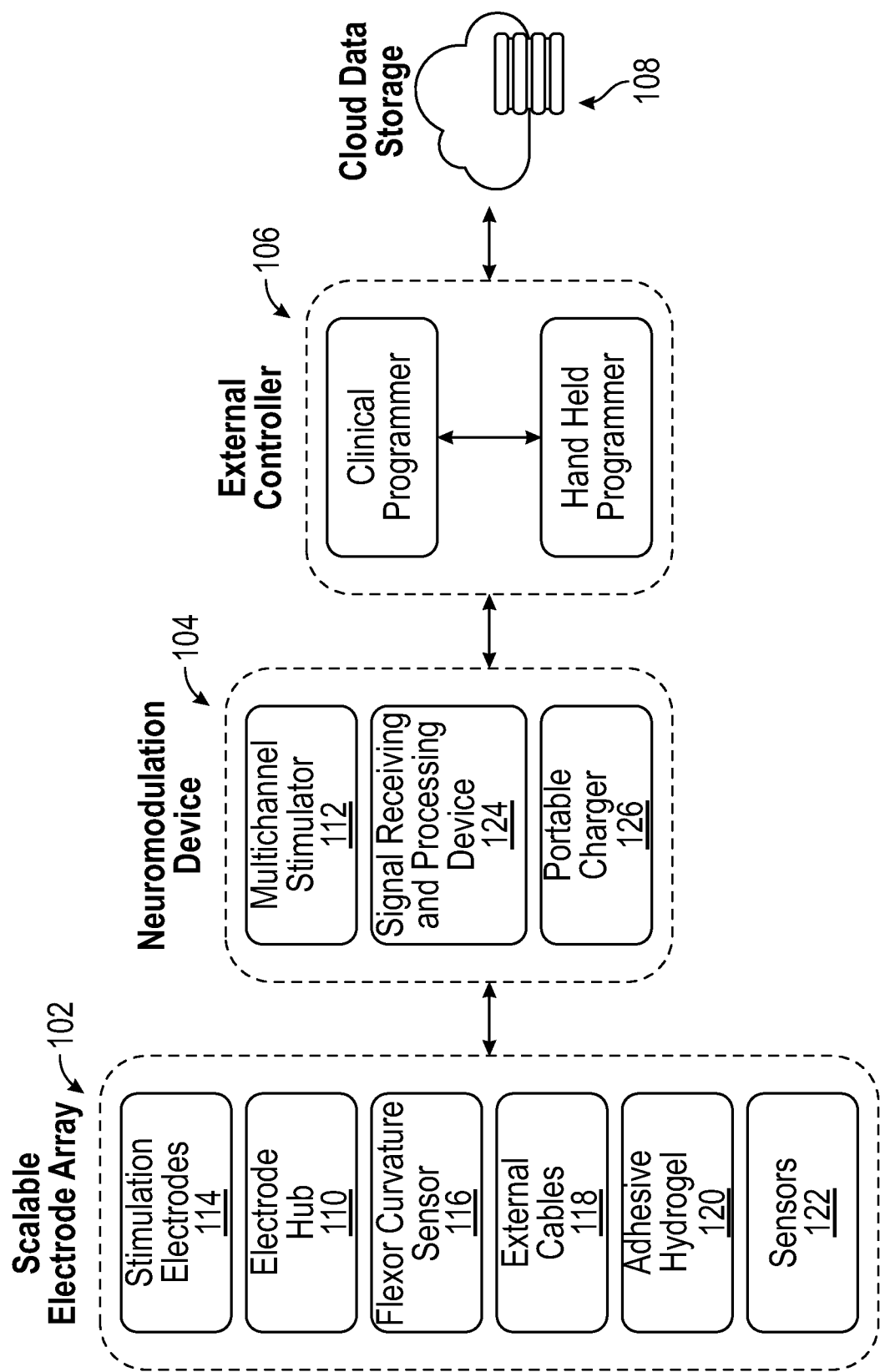
FIG. 1 shows a system block diagram highlighting various components of a non-invasive neuromodulation system.

A transcutaneous electrical stimulation system is provided, comprising a plurality of electrodes configured to be in contact with a skin surface of a patient, a flexible hub electrically connected to the electrodes and configured to be in contact with the patient, a bend sensor disposed in the hub and configured to measure a curvature of the hub, a signal processing device electrically coupled to the plurality of electrodes and the bend sensor, the signal processing device being configured to change stimulation settings of the plurality of electrodes based on the curvature of the hub, a multi-channel stimulator comprising at least one stimulation channel for each of the plurality of electrodes, the multi-channel stimulator being configured to receive the changed stimulation settings from the signal processing device and deliver electrical stimulation at each stimulation channel through its corresponding electrode.

In one embodiment, the bend sensor is composed of one or more accelerometers, gyroscopes, magnetometers, inertial measurement units, or some combination thereof.

In one embodiment, the bend sensor is also configured to measure posture or movement.

In one embodiment, the system further comprises electrical connectors detachably connecting the electrodes, hub, and electronics.

In one embodiment, electrodes are arranged in both longitudinal and transverse direction relative to the spinal cord and ganglion roots in an array configuration.

In one embodiment, the diameter of the electrode are 1-2 cm, 2-3 cm, or 3-5 cm and the longitudinal and transverse inter-electrode distances are between 1 mm and 5 cm.

In one embodiment, two or more electrodes are configured to selectively stimulate the biological targets.

In one embodiment, the stimulation target is the spinal cord, spinal ganglion roots, sympathetic and parasympathetic nerves, peripheral nerves, or visceral organs.

In one embodiment, the stimulation target is a specific spinal column and specific nerves/roots originating or being innervated by the selected spinal column.

In one embodiment, the multi-channel stimulation is configured to enhance and focalize the electrical field or the tangential electrical field, or the derivative of the electrical field or the tangential electric field at the selected target or targets and minimize the electrical field, the tangential electric field, or the derivative of the electrical field in other locations.

In one embodiment, the system further comprises sensors for electromyography, skin temperature, heart rate, blood oxygenation, blood pressure, sweat concentration, muscle hemodynamics, or a combination thereof.

In one embodiment, the curvature signal from the hub is used to dynamically restrict stimulation intensity to sub-motor threshold levels.

In one embodiment, the electromyography sensor is configured to detect sub-motor muscle activation during stimulation for the purposes of reducing skin irritation or is configured to detect reflex signals at selected muscles.

In one embodiment, the system further comprises one or more ultrasounds transducers connected to the outputs of the multi-channel stimulator and configured to deliver ultrasound stimulation to patient.

A transcutaneous electrical stimulation system is also provided, comprising a plurality of electrodes configured to be in contact with a skin surface of a patient, a muscle hemodynamics sensor based on near-infrared spectroscopy configured to be in contact with the skin surface of a patient, a signal processing device electrically coupled to the plurality of electrodes and the muscle hemodynamics sensor, the signal processing device being configured to change stimulation settings of the plurality of electrodes based on measurements from the sensor, a multi-channel stimulator comprising at least one stimulation channel for each of the plurality of electrodes, the multi-channel stimulator being configured to receive the changed stimulation settings from the signal processing device and deliver electrical stimulation at each stimulation channel through its corresponding electrode.

In one embodiment, the muscle hemodynamics sensor contains one or more infrared light emitting diodes and one or more photodetectors in contact with the skin surface of the patient.

In one embodiment, the light emitting diodes are configured to emit light at various wavelengths, each wavelength being associated with a different penetration depth and thus a different muscle unit.

In one embodiment, the light emitting diodes and photodetectors are contained inside a flexible hub.

In one embodiment, the system further comprises sensors for bending, electromyography, skin temperature, heart rate, blood oxygenation, blood pressure, sweat concentration, or a combination thereof.

In one embodiment, the signal processing device is configured to dynamically vary the stimulation amplitude based on measurements from the muscle hemodynamics sensor such that the stimulation amplitude is maximized while remaining under the motor threshold level.

An electrode hub of an electrode array is provided, comprising a flexible body, a plurality of electrical conductors supported by the flexible body and configured to transmit a neurostimulation pulse, a plurality of electrical connectors each communicating with at least one electrical conductor and each adapted to detachably connect to one or more electrodes, and at least one sensor configured to measure a curvature of the flexible body, the at least one sensor being supported by the flexible body and configured to communicate with a signal receiving and processing device.

In one embodiment, the sensors consist of gyroscopes, accelerometers, magnetometers, or a combination thereof.

An electrode for transcutaneous neurostimulation is further provided, comprising a central area comprising an electrically conductive solid material, the electrically conductive solid material being configured to attach to skin of a patient; an outer area disposed outside of the central area comprising an electrically conductive gel, and a peripheral area disposed outside the central area and the outer area and fully surrounding the electrically conductive solid material, the peripheral area being adapted to inhibit leakage current due to sweat from the skin of the patient.

In one embodiment, the peripheral area comprises a region with embedded chemical antiperspirant.

In one embodiment, the peripheral area comprises a highly electrically resistive material.

In one embodiment, the peripheral area contains electrically resistive microneedles which penetrate the skin and impede electrical current flow.

In one embodiment, the peripheral area comprises a liquid absorbent material.

An electrode array for transcutaneous neurostimulation is also provided, comprising a plurality of electrodes disposed on a substrate, each of the plurality of electrodes comprising a central area comprising an electrically conductive solid material, the electrically conductive solid material being configured to attach to skin of a patient, an outer area disposed outside of the central area comprising an electrically conductive gel, and a peripheral area disposed outside the central area and the outer area and fully surrounding the electrically conductive solid material, the peripheral area being adapted to inhibit leakage current due to sweat from the skin of the patient.

In one embodiment, the electrically conductive gel covers the electrically conductive solid material.

A method for ensuring repeatable and consistent placement of skin electrodes on a patient is provided, the method comprising acquiring an image of a patient, determining an outline of the patient and of major anatomical features of the patient, calculating an optimal placement of one or more electrodes on the patient to provide transcutaneous stimulation to the anatomical features of the patient, displaying the image of the patient, and displaying a location of the one or more electrodes as an overlay on the image of the patient.

In one embodiment, the image of the patient is acquired in real time and the calculated optimal placement of the one or more electrodes are superimposed on the patient's body and are constantly updated.

In one embodiment, the image of the patient is acquired by the camera of a tablet or mobile device and the image of the patient with overlaid electrodes is displayed on the screen of said tablet or mobile device.

A circuit for discharging the residual charge on an electrode is provided, comprising a discharge component adapted to be activated using non-electrical energy, and which is connected to the electrode and to a discharge path, a circuit adapted to deliver timed control energy to the discharge component and circuitry, an energy delivery circuit configured to deliver an electrical stimulation pulse to the electrode, and a control component or circuitry adapted to synchronize the energy delivery circuit with a stimulation pulse such that the discharge component activates to discharge the residual charge on an electrode without interfering with the stimulation pulse.

In one embodiment, the non-electrical energy is composed of light.

In one embodiment, the light is used to turn on a photodiode which then generates current to activate a discharge switch.

A method of discharging an electrode is provided, comprising the steps of generating electrical stimulation with the electrode that results in a residual charging building on the electrode, producing a first control signal after generating the electrical stimulation, converting the first control signal to a non-electrical signal with a first transducer, converting the non-electrical signal to a second control signal with a second transducer, activating a discharge component of the electrode with the second control signal to discharge the residual charge on the electrode.

In one embodiment, the non-electrical signal comprises light, pressure wave, ultrasound, or mechanical force, and the second transducer comprises a transducer specific to the non-electrical signal which converts the non-electrical signal to an electrical current to activate a discharge switch.

A method for transcutaneously stimulating a target nerve is provided, the method comprising the steps of delivering a plurality of short phases which increase to a target amplitude, delivering a single phase that is longer than the plurality of short phases, delivering a second plurality of short phases after the single phase with amplitudes decreasing from the target amplitude to zero, immediately repeating the preceding steps with the opposite polarity.

In one embodiment, the amplitudes of the short phases before and after the longer phase are determined by a sinusoidal function.

In one embodiment, the amplitudes of the short phases before and after the longer phase increase and decrease linearly.

In one embodiment, the width of each pulse can range from 10 μs to 10 ms, the stimulation frequency can range from 0 to 10 kHz, and the amplitude can range from −200 to 200 mA.

In one embodiment, the method further includes the following steps: Delivering a number of independent signals of the form stated above to the skin using an array of electrodes in order to mimic a physiological neural signal.

In one embodiment, the method further includes the following steps: Deliver a single short pulse for electrode-tissue impedance measurement.

In one embodiment, the method is applied to two or more electrodes concurrently to steer current to a specified biological target with a specified strength of electric field or its derivative.

A method for calibrating a transcutaneous spinal cord stimulation device is provided, the method comprising the following steps: applying two or more transcutaneous stimulation electrodes to a patient's skin near a spinal cord of the patient, applying one or more sensors to a target muscle group to detect a physiological response indicative of stimulation, for each of the two or more transcutaneous stimulation electrodes, delivering a series of pulses of increasing amplitude while recording measurements from the one or more sensors, recording an amplitude at which the one or more sensors detected measurements reaching a first predetermined threshold, for each of the one or more electrodes, delivering a series of pulses of decreasing frequency at the recorded amplitude while recording measurements from the one or more sensors, recording a frequency at which the one or more sensors detected measurements reaching a second predetermined threshold, and determining an anatomical location and distance from the spinal cord for each of the two or more transcutaneous stimulation electrodes based on the detected measurements from the one or more sensors.

In one embodiment, the sensors measure one or more of PRM reflexes, electromyography amplitudes, and latencies.

In one embodiment, the stimulation frequency is automatically decreased until a subject's perception threshold is reached.

In one embodiment, the stimulation frequency is automatically decreased until a patient experiences paresthesia.

In one embodiment, the rate of frequency modulation is according to a logarithmic rate.

A method of implementing safety controls for neurostimulation is provided, the method comprising applying a small current pulse to an electrode, measuring a voltage generated on the electrode during the small current pulse, calculating an impedance value from the measured voltage, determining if the impedance value falls within a specified range of values, and providing a stimulation pulse only if the impedance does fall within the specified range of values.

In one embodiment, the range of values is defined by an upper bounds value and a lower bounds value.

In one embodiment, the upper and lower bounds values are determined through a user input to a graphical user interface.

In one embodiment, this method is employed before each therapeutic stimulation pulse.

A method for implementing safety controls for neurostimulation is provided, the method comprising receiving a maximum overall current stimulation limit from a user, calculating an optimal stimulation parameters of each electrode in an electrode array to achieve focused stimulation of a target physiological structure, summing a stimulation current for each electrode and comparing it to the maximum overall current stimulation limit, and if the sum of the stimulation currents exceeds the maximum overall current stimulation limit, adjusting a stimulus firing timing to ensure that at any given time an overall stimulation current of the electrode array does not exceed the maximum overall current stimulation limit.

In one embodiment, the stimulus firing timing is adjusted using an algorithm which constructs a firing sequence by minimizing the root mean square difference of frequency between the user defined parameters and the fired parameters while ensuring that the combined amplitude does not exceed the maximum overall current stimulation limit at any moment in time.

In one embodiment, fired parameters are randomly generated and evaluated to find an optimized set of parameters.

A method of providing transcutaneous electrical stimulation to modulate the nervous system of a subject is provided, the method comprising: placing one or more electrodes in contact with the skin surface of a subject above a stimulation area; attaching the electrodes to a flexible hub containing sensors for measuring curvature, specifying the stimulation targets, estimating/calculating the stimulation configuration for each channel to perform focused stimulation, providing a first electrical stimulation therapy through at least some of the electrodes to perform selective stimulation; measuring the curvature of the flexible hub and physiological sensors, and providing a second stimulation therapy through at least some of the electrodes, a difference between the first stimulation therapy and the second stimulation therapy being based on a measured change in the hub's curvature and sensors readout.

In one embodiment, the neuromodulation is employed to facilitate upper limb function.

In one embodiment, the neuromodulation is employed to enable back posture control.

In one embodiment, the neuromodulation is employed to improve bladder control.

In one embodiment, the neuromodulation is employed for pain suppression.

In one embodiment, the neuromodulation is employed for autonomic nerves system modulation.

In one embodiment, the neuromodulation is employed to target a neural network incorporating multiple segments and specific targets concurrently or sequentially or randomly.

In one embodiment, the method further includes the following steps: placing one or more electrodes and one or more sensors on the subject's skin, stimulating the subject's skin with the one or more electrodes during a first stimulation, measuring an output of the electrodes during a first stimulation with the one or more sensors; adjusting at least one stimulation parameter of the one or more electrodes based on the measured output, stimulating the subject's skin with the one or more electrodes during a second stimulation.

DETAILED DESCRIPTION

As will be appreciated by consideration of the descriptions that follow, embodiments of the transcutaneous stimulation system and associated components described herein enable both selective stimulation at appropriate timings (i.e., spatiotemporal stimulation) and the modulation of a broader spinal network using non-invasive neuromodulation, both of which are of significance to improving the treatment effectiveness. Still further, aspects of the present disclosure relate to systems, devices, and methods for applying transcutaneous electrical stimulation with high spatiotemporal resolution, specifically for transcutaneous spinal cord stimulation. One objective of the inventive systems and methods described herein is to provide a non-invasive dynamic neuromodulation system for targeted and coordinated neuromodulation of the spinal cord and neural networks directly and indirectly connecting to the spinal cord of a subject. Systems and methods described herein can include one or more or combinations of the following:

1) embedded multi-modal sensors configured to sense the subject's physiological and physical signals, operatively connected with:
2) a signal receiving and processing device configured to receive signals from the user and the sensors and capable of executing signal analysis and processing algorithms, operatively connected with:
3) a non-invasive modular-designed multi-channel stimulator configured to receive stimulation commands from the signal receiving and processing device and capable of delivering independently configurable and dynamic stimulus at each individual stimulation channel, operatively connected with:
4) scalable non-invasive electrode arrays configured to cover a portion or multiple portions of the spinal cord and the associated neural networks connecting to the spinal cord to provide selective and focused stimulation at the desired firing timing, operatively using:
5) systems, methods, algorithms, and techniques to perform non-invasive stimulation with high selectivity and focality.

Key features can include 1) eliminating the need to re-adapt electrode positions to find optimal stimulation locations through multiple electrode arrays, 2) integrating physiological feedforward and feedback signals into a control loop for spinal cord stimulation, such as spine and limbs curvature feedback for posture-adaptive stimulation and hand torso sensing for upper limb control stimulation, 3) delivering versatile and flexible current output to multiple independent channels through specifically designed multi-modal signal transduction circuitry (as opposed to commercial stimulators which are only able to deliver tonic stimulation), and 4) delivering focused stimulation through current steering and electrical field shaping to the selective target (e.g., spinal ganglions, spinal column, and other nerves of interest) at appropriate timing. Many aspects of the disclosure can be particularly advantageous for various clinical applications, such as the non-limiting examples of: 1) the neuromodulation of cervical spinal circuitry for upper extremity rehabilitation, pain suppression, and autonomic function regulation (e.g., blood pressure, cardiac function, immune system function, urinary function, and gastrointestinal function), 2) the neuromodulation of thoracic or lumbosacral spinal circuitry for gait therapy, bladder control, chronic pain management, and gastrointestinal function, and 3) selective stimulation of the sciatic nerve for regulation of white and red blood cell counts, and 4) stimulation of immune system circuitry residing in the spinal networks. Furthermore, additional other aspects of the disclosure can be utilized for neuro-diagnostic testing for spinal cord injury patients, such as 1) assessing the symmetry intactness of nervous tract though unilateral evoked posterior roots muscle (PRM) reflexes, and 2) conducting non-invasive testing for patient eligibility of epidural spinal cord implant surgery.

FIG. 1 shows a system block diagram highlighting various components of a non-invasive neuromodulation system according to one embodiment. These components can be subdivided into four categories: a) one or more scalable electrode arrays 102; b) a neuromodulation device 104; c) an external controller 106; and d) cloud data storage 108.

Figure 2B:
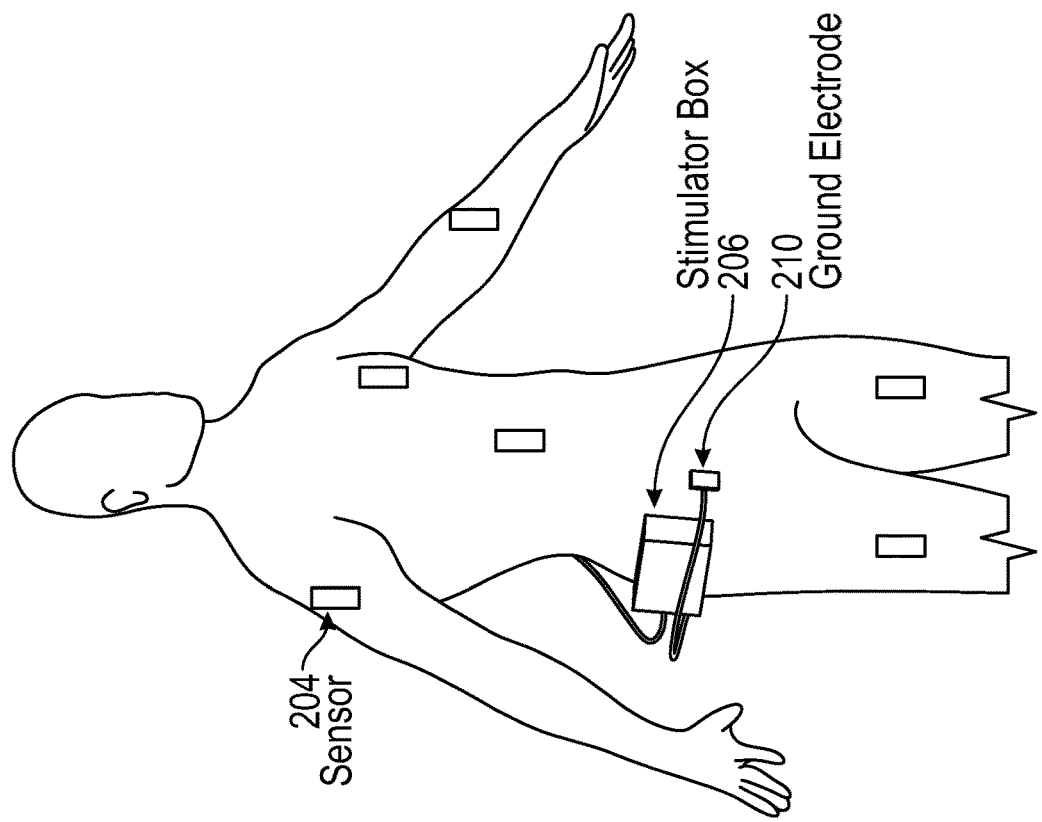
FIGS. 2A-2B show an example of how the device may be worn and carried by the patient during use.
Figure 2A:
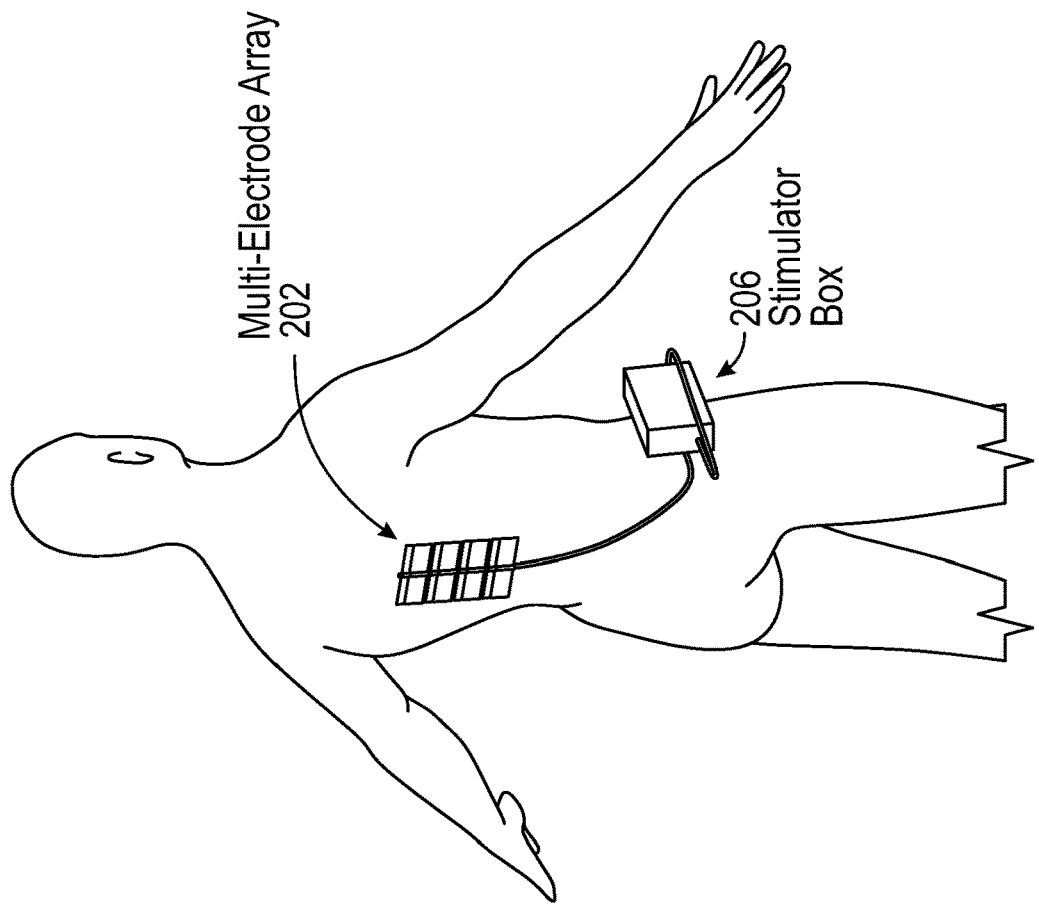

FIGS. 2A-2B show an example of how the device may be worn and carried by the patient during use. The multielectrode array may be adhered to the patient's back 202 and connected to the stimulator box 206 through a flexible cable. A ground electrode 210 may be connected to the stimulator box 206 through a separate flexible cable and adhered to the patient; in one embodiment, the ground electrode may be attached to the patient on the skin above the iliac crest. In one embodiment, a plurality of sensors 204 may be adhered to the patient's skin at various locations around the body. In another embodiment, the portable stimulator 206 can be carried near the user's abdominal area (e.g., hooked on user's belt), but it may be placed or carried in other ways.

In one embodiment, referring back to FIG. 1, the scalable electrode array(s) 102 includes one or more or a combination of design features, such as for example, 1) at least one flexible electrode hub 110 which links a multi-channel stimulator 112 of the neuromodulation device 104 to a plurality of stimulation electrodes 114, 2) an embedded flex or curvature sensor 116, 3) electrode arrays which relay electrical current between the hub and a plurality of independent electrodes of varying size and inter-electrode gap, 4) external cables 118, and either 5a) disposable adhesive hydrogel snap electrodes, or 5b) adhesive hydrogel strips.

The flexible hub 110 provides an interconnection solution to simultaneously connect multiple stimulation electrodes or electrode arrays 114 in a modular way. Unlike traditional discrete wiring that is unorganized and prone to tangling, embodiments of the present disclosure provide all the required interconnections for multi-channel systems through a flexible electrode hub 110 coupled to the plurality of stimulation electrodes or multi-electrode arrays. The hub and the electrodes can be adhered to the subject's skin (e.g., via adhesive hydrogel 120) for simultaneous stimulation and recording from various spatial locations on the human body for various clinical applications. The flexible hub can further embed one or more sensors 122. In one embodiment, the one or more sensors 122 include at least one sensor configured to monitor body and limb posture and/or spine curvature. In another embodiment, the sensors 122 can further include sensors configured to measure parameters of the user or patient. These sensors can be standalone sensors attached to the electrode hub, or alternatively, the sensors can be integrated into the hub or into the electrodes themselves. Biocompatible adhesive hydrogel can be applied to the hub with integral strain sensor in order to be attached to the human body without potential irritation and tissue damage.

The presented modular electrode design facilitates electrode replacement by substituting deteriorated units with new units. Further, electrode size and inter-electrode gap can be modified to optimize treatment efficacy. In some applications, electrodes with different sizes can be attached to or manufactured at the same array. In an example embodiment, the size and pitch of the electrodes for cervical and lumbosacral spinal stimulation would be different due to its anatomic difference. The electrode size can range from 1 cm to 5 cm, and the longitudinal and transverse inter-electrode distance is between 1 mm and 5 cm. The electrode array can be used for cervical, thoracic, or lumbosacral non-invasive spinal stimulation to stimulate the underlying spinal circuitries and network. In one embodiment, the current intensity, polarity, and firing timing at each electrode can be independently adjusted to steer the stimulation current to the target (e.g., spinal column and spinal ganglion). When using the electrode array, any electrode among the array can serve as the ground electrode; one or multiple ground electrodes can be placed on the abdominal wall or the iliac crest of the patient.

In another embodiment, multiple sets of the electrode arrays can be arranged to stimulate multiple spinal segments in a coordinated and selective order at the same or different frequencies. In particular, at least one electrode in each array can be used to deliver current to the targets through a selective temporal and spatial configuration of the electrodes and stimulation parameters. In addition, when needed, the multiple electrodes can be combined to share the same stimulation channel or multiple electrodes can be used to deliver the same or different stimulation parameters concurrently from independent stimulation channels. External cables link the flexible hub and integral strain sensing to the neuromodulation device.

The neuromodulation devices described herein can comprise a battery-powered, portable, multi-channel stimulator 112 that links to the scalable electrode array, a signal receiving and processing device 124, and a portable power charger 126. The stimulator can contain stimulation electrical circuitry, a power source, signal receiving and processing device, and can be connected to an accompanying mobile graphical user interface. In one embodiment, the signal processing device amplifies, digitizes, filters, and stores the recorded physiological signal; feature extraction and signal dimension reduction are then performed to derive features most related to the desired patient outcome (e.g., the curvature of the spine that represents the trunk posture of the subject; a patient-specific amplitude of EMG or optical sensor readout that represents the required force generated by the muscle of interest for a specific motor task). These features are deemed as patterns and can be continuously updated (i.e., trained) as characteristics of the recorded physiological signal varies with time (e.g., EMG is a non-stationary signal). These features can be used as benchmarks to optimize stimulation parameters for achieving the desired patient outcome.

Each channel of the stimulator can connect to at least one of the independently controlled electrodes. Each channel of the stimulator can be configured to deliver stimuli synchronously and asynchronously with different stimulation parameters for each individual channel. The delivered stimuli can be synchronous and asynchronous waveforms made of combination of single or multiple monophasic and biphasic stimuli. Such stimulation steers the electrical charge to the desired targets, resulting in stimulation with high specificity through precise control of the stimulation current and timing. The intensities of stimuli at each individual channel can be derived by incorporating a realistic human model and stimulation optimization methods, such as a maximum intensity method, a linear constrained minimum variance method, or a tSCS optimization method designed for transcutaneous stimulation. In particular, such stimulation can be conducted to enhance the electrical field or the derivative of the electrical field at the desired targets, or to enhance the tangential electric field (i.e., electrical field in x, y, or z direction) or derivative of the electric field or the tangential electric field at the desired targets. In particular, the tangential electric field components can be extracted from the original electric field.

The focused and selective non-invasive neuromodulation can be used to modulate the nervous systems that regulate the motor function, immune function, pain treatment, gastrointestinal function of stomach, intestine and colon, bowel function, bladder function, sexual function, and/or cardiovascular function by targeting different nerve segments. In particular, the focused neuromodulation modulates the spinal segment or ganglion roots that governs specific muscles, nerves, or network for specific task, or neuronal networks that directly and indirectly links to the spinal cord. In particular, the said neuromodulation device can modulate the spinal networks and specific spinal segment or ganglions simultaneously by applying one set of stimulation parameters to tune the network and another set of stimulation parameters to activate or suppress specific nerves of interest concurrently or sequentially.

The signal receiving and processing device 124 is configured to sense and monitor signals from the user, including but not limited to heart rate, electrocardiogram, electromyography, photoplethysmogram, sweat electrolytes, motion kinetics, motion kinematics, blood pressure, walking speed, muscle activation, and bio-impedance. The signals can be received, for example, from sensors 122 that are integrated within or attached to the hub 110, integrated within the electrodes, and/or coupled to the patient or user. Each sensor can be implemented through off-the-shelf electrodes, sensor chips, microcontrollers, field-programmable gate arrays (FPGA), telemetry systems, or power sources. The recorded sensor data can be transmitted to the signal receiving and process device and the external controller as biofeedback to 1) improve stimulation efficacy and optimize stimulation parameters, and 2) ensure user safety related to stimulation parameters.

The external controller 106 comprises a portable clinical/user programmer for bi-directional telemetry communication with the neuromodulation device and processing the recorded sensor data to estimate and determine the stimulation parameters (i.e., the firing timing, pulse width, frequency, intensity, and polarity, and the electrodes to be activated). In addition to configuring the stimulation parameters or stimulation program, the external controller is configured to record and broadcast the recorded signal to the cloud storage for data storage, processing, analysis, and visualization. The uploading procedure can take place at the time when the patient is not using the device for delivering stimulation or under the circumstance that an emergent signal needs to be sent to the caregiver. In another embodiment, the external controller is configured to record the stimulation timing and duration, parameters, electrode configuration, and the pre-stimulation calibration procedure performed to map electrode placement for optimal stimulation sites. In another embodiment, the external controller is configured to record the electrode configuration by documenting electrode placement on the subject to ensure the electrode is placed on the identified spot for ensuing stimulation. An augmented reality (AR) transparent layover enabled by a camera coupled to the external controller may be used to aid in repeatable electrode placement; alternately, the controller could employ algorithms to identify the outline and major anatomical features of a subject using the coupled camera and inform the user of the correct placement through a graphical user interface.

Another objective of an aspect of this disclosure is a method for facilitating the upper extremity motor and sensing function in a subject in need through combinations of one or more steps, such as the following steps:
1) place one or multiple electrode arrays on the skin above the cervical and lumbosacral spinal segments;
2) place sensors on the subject's upper back, lower back, arms and shoulders;
3) specify the stimulation targets, estimate/calculate the stimulation setting for each channel to perform current-steering targeted stimulation using the said signal receiving and processing device;
4) send the recorded signal from the sensors to the signal receiving and processing device and the external controller;
5) provide and change the stimulation settings to the stimulator based on the recorded signal from the sensors to deliver multi-channel stimuli with independently configurable parameters at each channel;
6) deliver electrical charge to the subject with at least one electrode array attached at a selective firing timing to the specified target or targets.

Selective firing timing refers to the delivery of stimulation at spinal segments or related nerves that govern upper limb function in a precise order. This order may be sequential (e.g., C5-C6-C7C8-T1-T2), nonsequential (e.g., C5-T1-C8-C7-C6-T2), or random.

A further objective of an aspect of this disclosure is a method and non-invasive neuromodulation system for the trunk muscle control in a subject in need to facilitate sitting, comprising:
1) a neuromodulation system as defined and described above;
2) sensors to sense the posture and spine curvature in real-time;
3) a signal receiving and processing device receives the sensed signal and executes a real-time signal analysis to change and transmit stimulation settings;
4) a multi-channel stimulator receives the stimulation parameters settings and deliver the stimuli to the subject through the one or more electrodes arrays on the cervical and lumbosacral spinal segments at selective timing.

Another objective of an embodiment of this disclosure is a method for the bladder regulation in a subject in need, comprising:
1) a neuromodulation system as defined and described above;

2) stimulation settings calculated based on the spinal cord targets using the signal receiving and processing device, preferably the target is the L1-2 and S1-2 spines and associated spinal roots that regulate the bladder function;
3) the said settings are transmitted to the stimulator to selectively stimulate the targets at the same time or at selective timings.

Another further objective of an embodiment of this disclosure is a method for pain suppression/treatment in a subject, comprising:
1) a neuromodulation system as defined and described above;
2) selection of the spinal target based on the origin of the pain;
3) stimulation settings calculated based on the spinal cord targets using the signal receiving and processing device and the said target is the afferent neuron or dorsal roots to the spinal cord that conveys the sensory input to the brain;
4) delivering the stimuli to the target through the electrode arrays.

Another further objective of an embodiment of this disclosure is a method for regulating the immune system in a subject, comprising:
1) a neuromodulation system as defined and described above;
2) selection of the target based on the function of the nerve or spinal segments;
3) stimulation settings calculated based on the selected targets and the said target is the sympathetic and parasympathetic nerves and spinal dorsal roots;
4) delivering the stimuli to the target through the electrode arrays.

Another further objective of an embodiment of this disclosure is a method for regulating the gastrointestinal system in a subject, comprising:
1) a neuromodulation system as defined and described above;
2) selection of the target based on the function of the nerve or spinal segments;
3) stimulation settings estimated based on the selected targets and the said target is the sympathetic and parasympathetic nerves and spinal dorsal roots;
4) delivering the stimuli to the target through the electrode arrays.

A further objective of an aspect of this disclosure is a method and non-invasive neuromodulation system for the autonomic control in a subject, comprising:
5) a neuromodulation system as defined and described above;
6) sensors to sense heart rate, blood pressure, sweat, and skin impedance in real-time;
7) a signal receiving and processing device receives the sensed signal and executes a real-time signal analysis to change and transmit stimulation settings;
8) a multi-channel stimulator receives the stimulation parameters settings and deliver the stimuli to the subject through the one or more electrodes arrays on the cervical and lumbosacral spinal segments at selective timing.

Details of the neuromodulation system are described in the following:

1. Flexible Hub with Embedded Sensing Elements

Figure 3:
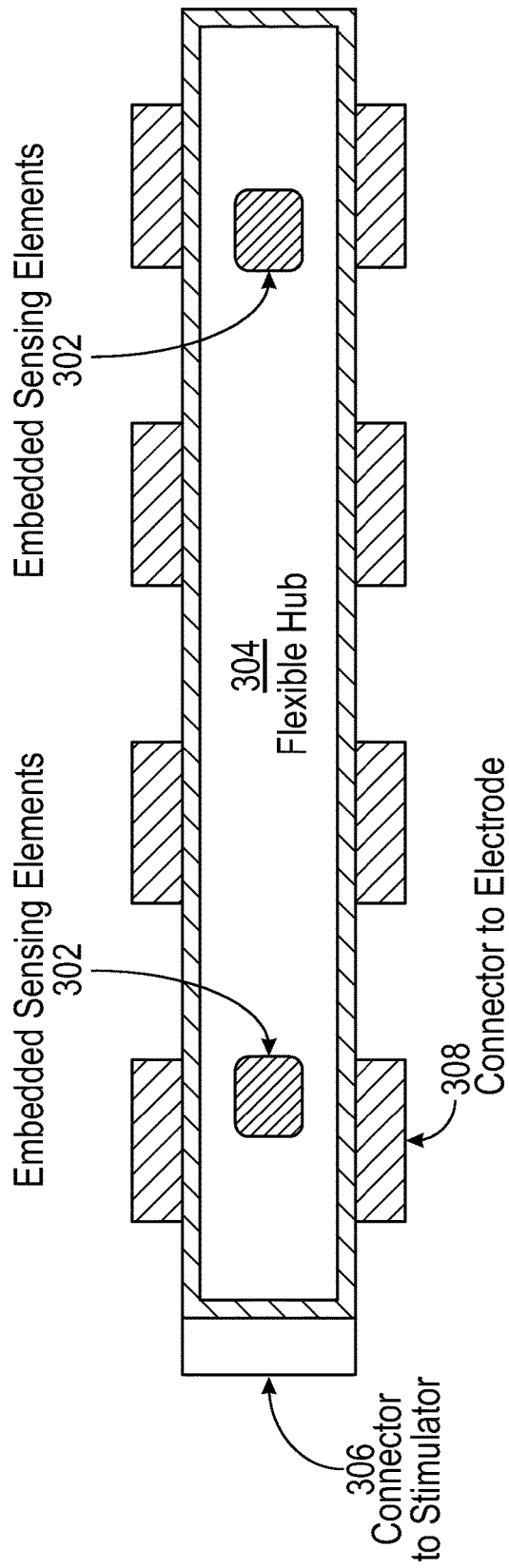
FIG. 3 shows one embodiment of a flexible hub of an electrode array.

As shown in FIG. 3, one embodiment of the disclosure provides an electrode array—the flexible hub 304. The hub functions to 1) relay electrical signals between the stimulator and scalable electrode arrays 308, and 2) measure spine curvature or body posture using embedded sensing elements. Using a centralized hub to connect electrodes to the stimulator 306 eliminates excess wires, adding convenience for the patient and significantly improving the electrode placement process for the physician. In addition, a central hub increases clinical effectiveness by allowing physicians the flexibility to place electrodes symmetrically or asymmetrical on either side of the spinal cord in a precise orientation. In addition to its role in relaying stimulation signals, the hub may contain one or more sensing elements 302 to monitor the physiological state of the patient, enabling closed loop neurostimulation.

Figure 4:
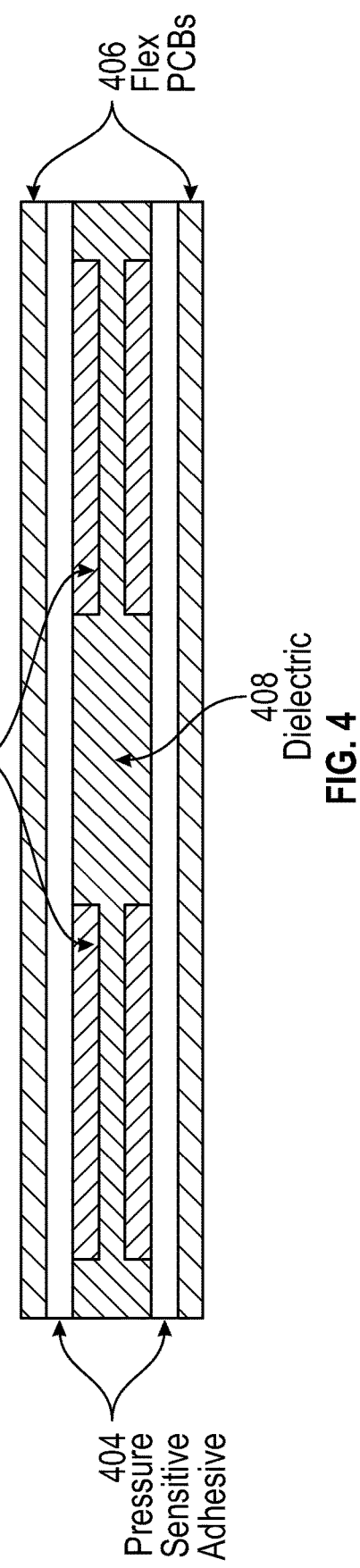
FIG. 4 shows an embodiment of a flexible hub with strain sensors.

In one example, these sensing elements can include inertial measurement units (IMUs) or strain sensors to measure spinal curvature, posture, and/or patient movement. In one example, a strain sensor may be integrated with the flexible hub by stacking one on top of the other. In one process for fabrication of the flexible hub, two or more multi-layer flexible printed circuit boards 406 are bonded together utilizing pressure-sensitive adhesive 404 or other adhesive materials, with a strain sensor made up of two or more capacitive sensing elements 402 between the circuits (FIG. 4).

The strain sensor can be structured as two or more capacitive sensors, each comprising two or more layers of conductive polymers, symmetrically separated by a layer of dielectric material. Resistive-based sensors can also be an implemented for the same application. In one embodiment of the present disclosure, the capacitive sensor is embedded in between two flexible or stretchable circuits, in order to minimize external localized mechanical strain and consequential hysteresis. In another embodiment, the strain sensor relays analog or digital signals is coupled to the neuromodulation device or the external controller through wired or wireless connection for further signal processing.

Figure 5:
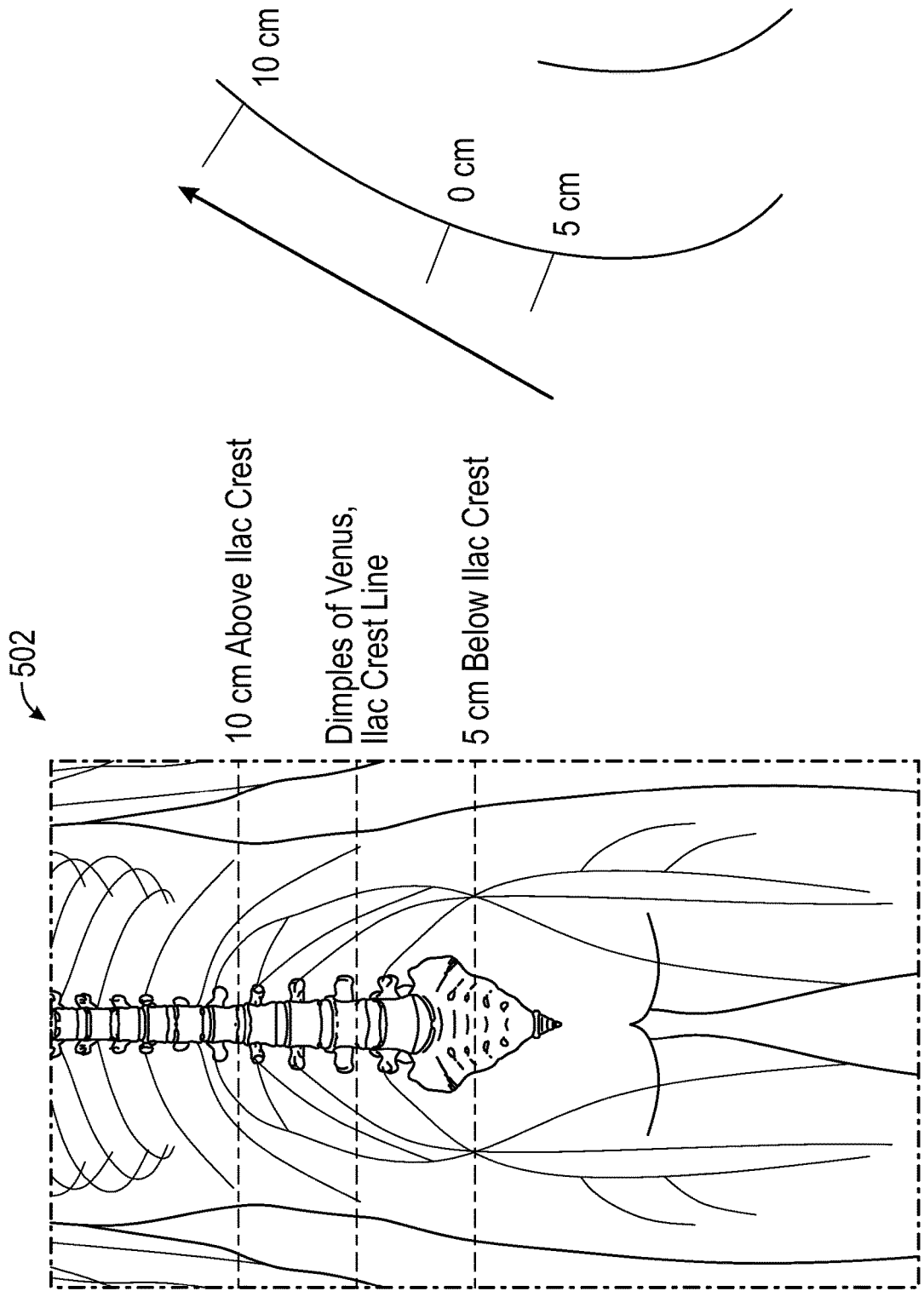
FIGS. 5A-5B demonstrate the typical variation in spine curvature that would normally occur if the user were not restricted to a single position, such as supine, prone, sitting or standing.

FIGS. 5A-5B demonstrate the typical variation in spine curvature that would normally occur if the user were not restricted to a single position, such as supine, prone, sitting or standing. During such posture variation, the activation thresholds of the dorsal sensory afferents, ventral motor efferents, and spinal cord neural circuits significantly shift due to variations in 1) electrode to spinal cord distance caused by skin movement, 2) thickness of cerebral spinal fluid (e.g., 50-100% as human body moves from supine to prone), 3) spinal cord position in the spinal canal, and 4) orientation of the neural fibers (e.g., transversal and longitudinal alignment of the sensory and motor neurons at spinal cord entry zone in the supine position favors sensory activation over motor activation).

One approach to monitoring body position is to use inertial measurement units (IMUs), which contain accelerometers, gyroscopes, and/or magnetometers to enable measurement of relative position, orientation, and movement. A single IMU could be used to determine patient activity and posture; the use of two IMUs could be used to measure spinal curvature via relative orientation between different locations above the spinal cord or measurement of arm position using orientation angles at multiple arm points. A complementary and robust method of measuring spinal curvature involves the use of a strain sensor embedded in the hub, which directly measures lumbar angle. The use of multiple sensing modalities would increase safety and accuracy of measurement; data from both devices could be combined using a Kalman filter or complementary filter before use in a closed-loop neurostimulation algorithm.

In addition to measuring body position, different embodiments of the hub could monitor other physiological signals useful for closed-loop control of stimulation parameters. These may include electromyography (EMG) signals, skin temperature, heart rate, blood oxygenation, blood pressure, or sweat concentration. EMG signals could be measured using EMG electrodes embedded in the bottom surface of the hub or attached via wires, skin temperature could be measured using a resistance temperature detector fabricated directly on the hub's flexible circuit board, heart rate, blood pressure, and blood oxygenation could be measured using light-emitting diodes and photodetectors in direct contract with the patient's skin through the bottom surface of the hub, and sweat concentration could be measured using a low-amplitude, high-frequency signal between two small electrodes on the hub. Any or all of these sensors could be included in various embodiments of the disclosure, depending on the specific needs of a patient.

The present disclosure provides devices that are configured to monitor the variation in physiological state in order to effectively and safely modulate the stimulation parameters. Spine curvature feedback is a useful feature to dynamically restrict stimulation intensity to sub-motor threshold levels. The user's motor thresholds are determined during the diagnostic or testing phases of therapy and subsequently used as pre-set parameters to minimize the likelihood of the occurrence for painful or twitch-inducing overstimulation.

EMG signals may be used to detect sub-motor muscle activation during stimulation, allowing the stimulator to slowly ramp up stimulation magnitude until muscle activation occurs. Such a ramp-like calibration process would reduce skin irritation due to high stimulation currents. In addition, EMG signals could be used to precisely focus the electric field by activating various patterns of electrodes while detecting reflex signals at the muscle under consideration.

Skin temperature and sweat concentration are both useful physiological signals for calibrating stimulation parameters because variations in either will change the electrical resistance of the skin. Precise knowledge of the sweat concentration and skin temperature allows accurate adjustment of stimulation magnitude and frequency, so that effective stimulation is delivered transcutaneously and leakage current is minimized.

Measurement of heart rate, blood oxygenation, and blood pressure will all significantly increase the safety of the patient during stimulation. Errant transcutaneous stimulation signals have the potential to interfere with or enhance conduction through the vagus nerve, which modulates several physiological processes including heart rate and blood pressure. Currently, physicians carefully monitor heart rate, blood pressure, and blood oxygenation during the initial placement of electrodes to ensure that stimulation does not affect these parameters; however, this method is time consuming and requires skilled medical personnel. Constant monitoring of these parameters would significantly improve patient safety and eliminate human error. Thus, one aspect of the present disclosure renders transcutaneous spinal cord stimulation as a more feasible option to use both in and out of the clinical setting and generates a wealth of physiological data to expand our understanding of the correlation between posture and therapeutic effectiveness.

Furthermore, in order to overcome stimulation artifact, which always overwhelms the recorded EMG signal, blood oxygenation in the muscle can be used as a biomarker to monitor the muscle response and can be measured by using Near Infrared Spectroscopy Sensor (NIRS). As an alternative to EMG, near infrared spectroscopy (NIRS) can be used to enable closed-loop stimulation using muscle hemodynamics as the feedback signal. The use of NIRS-based muscle hemodynamics for closed-loop feedback during transcutaneous stimulation has significant advantages over the use of EMG signals due to its immunity to stimulation artifacts presented in EMG during stimulation. In one embodiment, one or more standalone muscle hemodynamic sensors are placed on the skin above muscles of interest and connected to the stimulator. This connection between the muscle hemodynamic sensors and the stimulator could be through wired connections or could be mediated through a wireless protocol such as Bluetooth or WiFi. Alternately, the muscle hemodynamic sensor could be embedded in the electrode hub.

Figure 6:
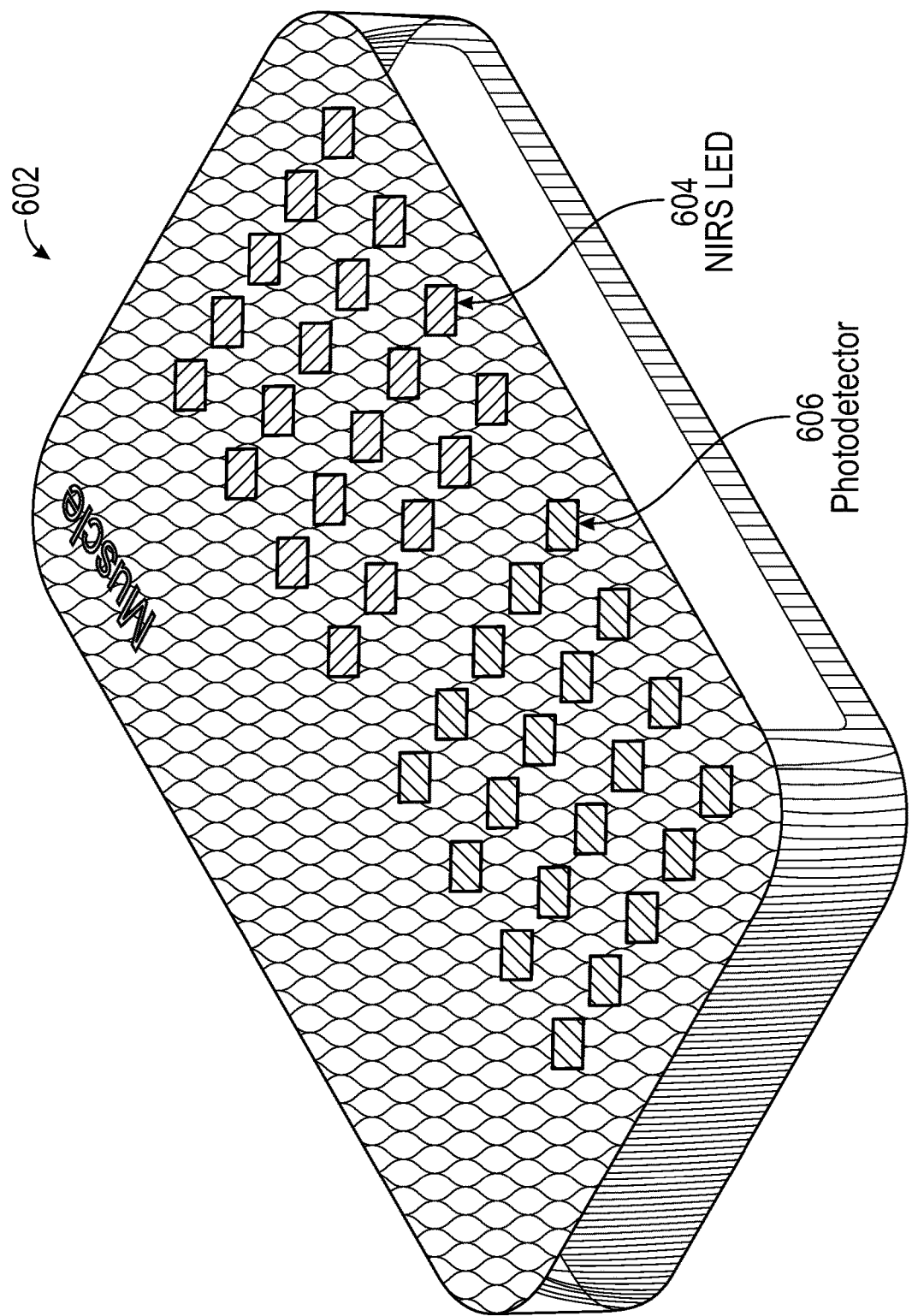
FIG. 6 shows one example of a muscle hemodynamic sensor including one or more near-infrared light emitting diodes (NIR LEDs) and one or more photodetectors placed on the muscle tissue.
Figure 7:
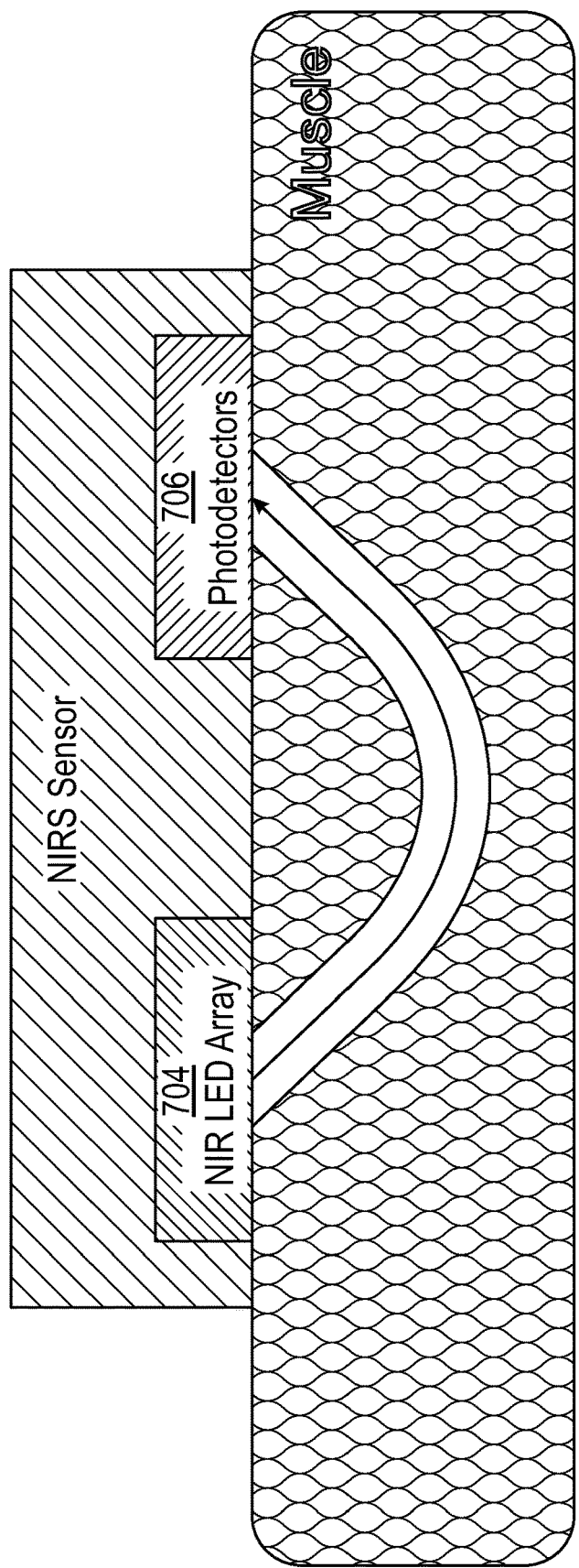
FIG. 7 is another view of a muscle hemodynamic sensor including NIR LEDs and photodetectors.

In one embodiment, referring to FIG. 6, the muscle hemodynamic sensor 602 comprises of one or more near-infrared light emitting diodes (NIR LEDs) 604 and one or more photodetectors 606 placed on the muscle tissue. FIG. 7 is another view of the sensor 702 including NIR LEDs 704 and photodetectors 706. The sensor 702 can include electronics configured to activate the NIR LEDs and process the signal from the photodetectors 706. The NIR LEDs 704 are configured to emit near-infrared light to the muscle while photodetectors 706 capture the light that passes through muscle tissue. The main absorbers during near-infrared light transmission in muscle tissue are blood chromophores of oxygenated hemoglobin ($HbO_2$) and deoxygenated hemoglobin (HHb) that indicates the muscle oxygenation states reflecting the muscle contraction and relaxation processes. Therefore, through measuring the intensity of the light passing to the photodetector, $HbO_2$ and HHb that contain hemodynamics information in muscle can be characterized. Different muscle units that are located at different depths can be characterized using NIR light with different penetration depth. The penetration depth is around a half times of the separation between NIR LED and photodetector. Multiple NIR LEDs and photodetectors could enable the detection of muscle units that are located at various positions and depths.

In one embodiment, the multiple NIR LEDs could be composed of LEDs with different wavelengths that emit with different parameters including intensity, duration, and turn-on time. In one embodiment, multiple photodetectors could be composed of different photodiodes that are sensitive to different wavelengths of light. In one embodiment, the photodiode could be replaced with a phototransistor or photoresistor.

To enable muscle hemodynamics sensing using NIRS, the muscle hemodynamic sensor may contain electronics such as a microcontroller or a field-programmable gate array (FPGA), LED driver circuitry, and analog circuitry for the photodetection. In a preferred embodiment, the LED driver circuitry is composed of a custom application specific integrated circuit (ASIC) that is capable of generating multiple channels of current with independent control of the magnitude, pulse duration, and turn-on time for each LED. In another embodiment, the current driving each LED may be independently controlled by a current source that is composed of a digital-to-analog converter (DAC), an operational amplifier (OPAMP), a p-MOS transistor, and a resistor. The feedback configuration of OPAMP enforces the current magnitude to be the output voltage of DAC divided by the resistor value. The DAC also controls the pulse duration and turn-on time of the current pulse for each LED. In a preferred embodiment, the photodetection circuitry consists of a photodiode and a transimpedance amplifier that is composed of an OPAMP, a capacitor, and a resistor. The transimpedance amplifier converts the current produced by the photodiode to a voltage that will be sent to the microcontroller or FPGA for signal processing.

2. Electrode Arrays

Figure 8:
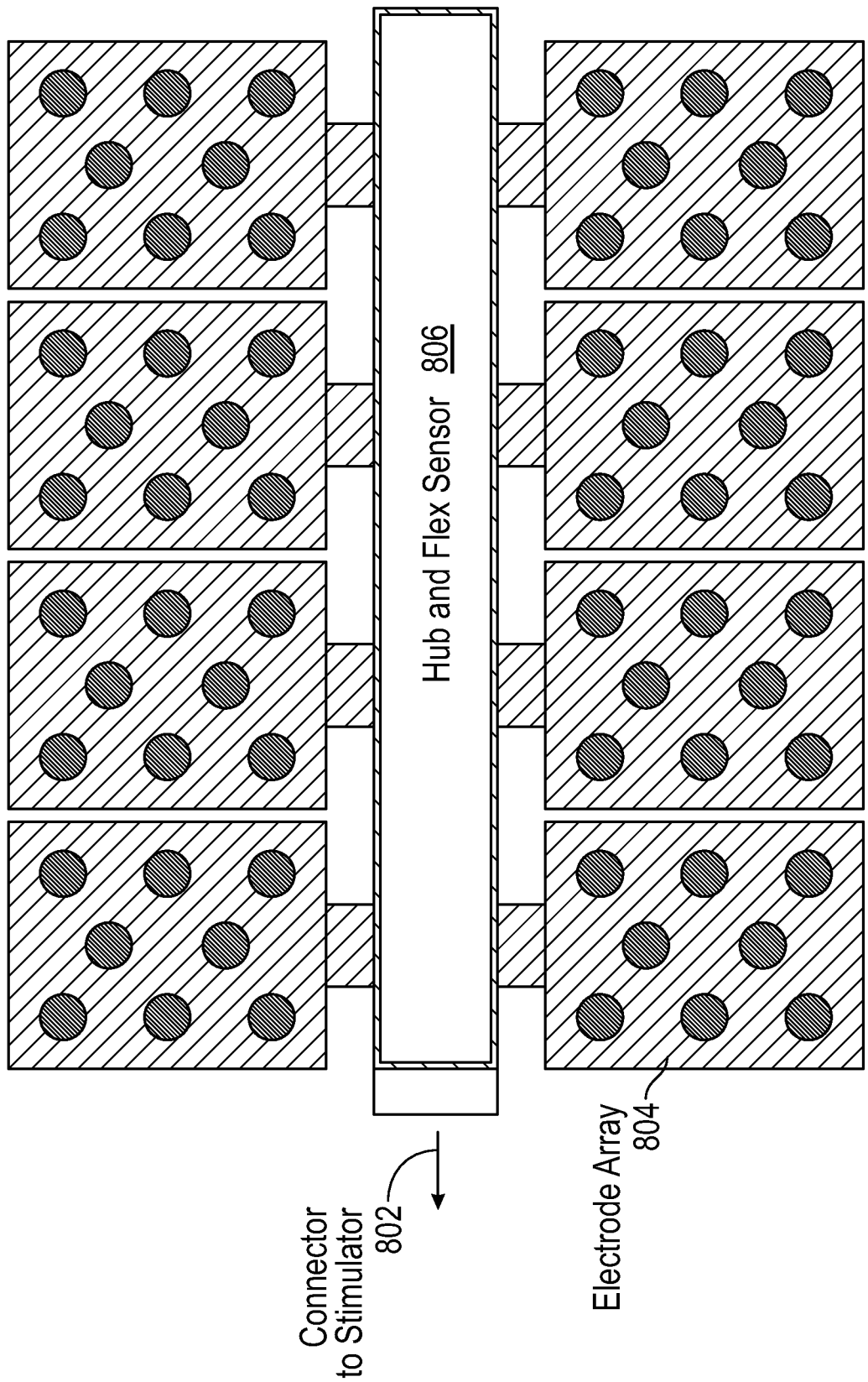
Figure 10C:
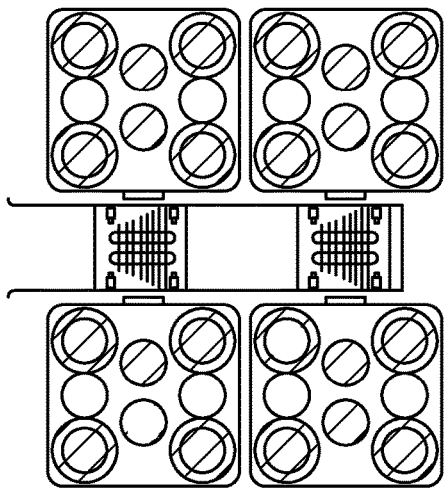
Figure 10D:
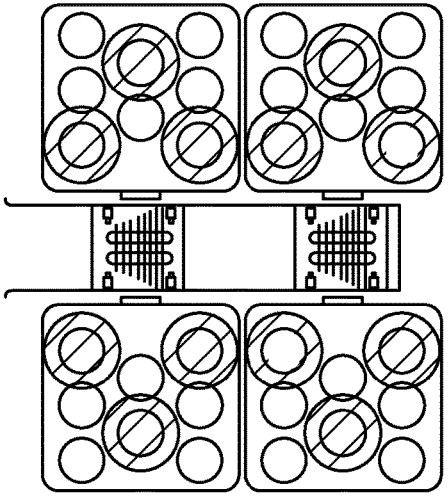
Figure 10A:
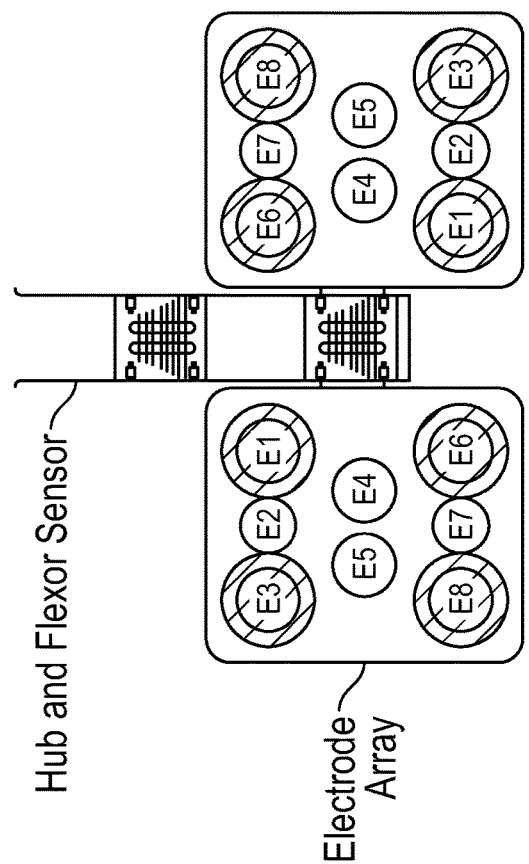
Figure 10B:
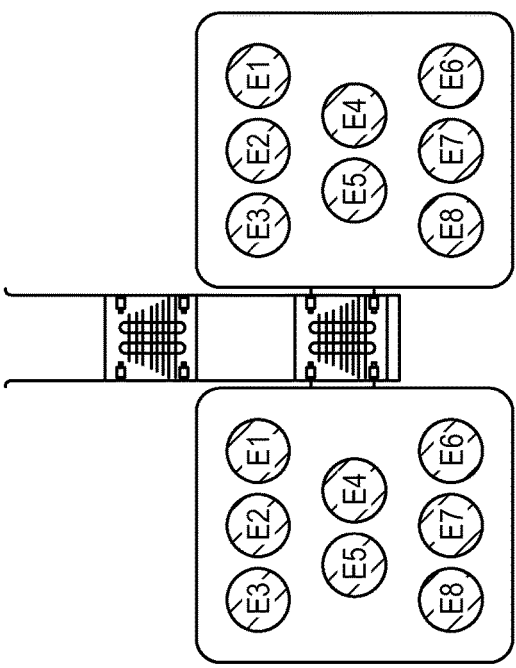

In FIGS. 8, 9A-9B, 10A-10D, and 11A-11C, various configurations of a flexible hub and electrode arrays are shown. Referring to FIG. 8, the flexible hub 806 connects to a plurality of electrode arrays 804. FIGS. 9A-9B, 10A-10D, and 11A-11C illustrate hubs having electrode arrays with different configurations and spatial layouts. Each electrode array embodies conductive traces to route electrical signals into a plurality of discrete or integrated independent electrodes of various sizes (e.g., 1 cm to 5 cm in diameter). In one embodiment, each array embodies at least mating connector pluggable into compatible connectors integral to the flexible hub.

Figure 12A:
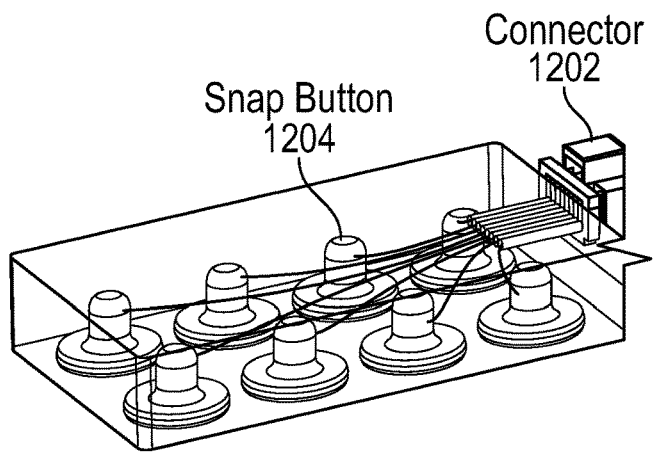
FIG. 12A illustrates one embodiment of an electrode array with traces that terminate in a snap button.
Figure 12B:
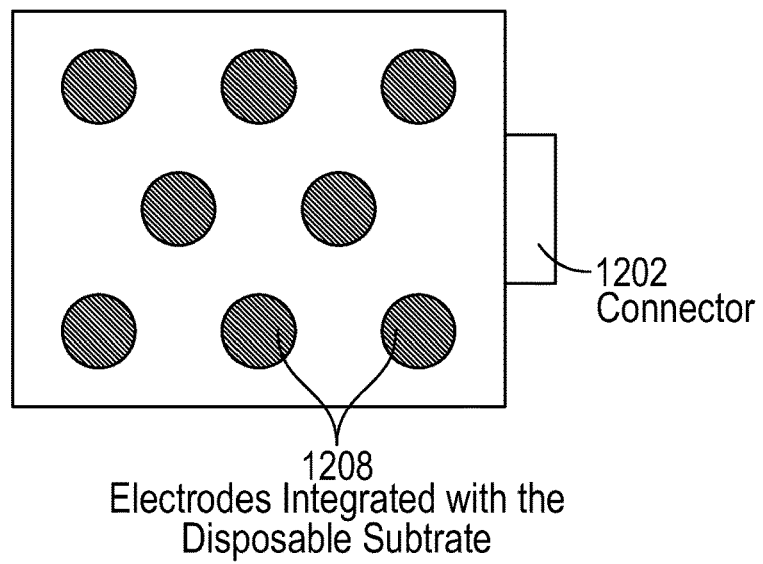
FIG. 12B is an embodiment of an electrode array that comprises a disposable patch.

In another embodiment, referring to FIG. 12A, the traces of the electrode array can terminate with female/male snap buttons 1204 on the bottom surface of the array, in order to be compatible with the male studs of common commercial snap electrodes. Under such, once the electrode is deteriorated, a replacement electrode can be used for substitution. A connector 1202 to the electrode array is also shown in FIG. 12A. In another embodiment, shown in FIG. 12B, the entire array can be a disposable patch with multiple electrodes being integrated together into the same substrate 1208. A connector 1202 to the electrode array is also shown in this embodiment.

In another embodiment, the electrode arrays are constructed by layering a specific pattern of conductive elements (e.g., silver ink, poly (3,4-ethylenedioxythophene) polystyrene sulfonate; PEDOT:PSS) onto a base dielectric substrate (PDMS, PET, polyimide, Parylene, foam, fabrics, etc.). Additive or subtractive fabrication techniques may be used to manufacture arrays comprising of a plurality of discrete or integrated electrodes (at least two electrodes), in accordance with the desired size and inter-electrode gap. For arrays with integral conductive electrodes, adhesive hydrogel can be applied over the array to form conductive elements. The hydrogel functions to 1) form various alternate geometries of skin-contacting virtual electrodes, and 2) improve the biocompatibility and adhesion strength of the skin-contacting material. Non-conductive hydrogel can be applied to the substrate to strengthen the adhesive force.

In one embodiment, each electrode array comprises eight 1 cm diameter round electrodes in 4×2 configuration with a horizontal gap of at least 2 mm and vertical gap of at least 5 mm. Such configuration ensures that at least one row of electrodes is closely placed on top of the targeted segment of inter-vertebrae, where most current flows into the spinal canal. In another embodiment, electrode arrays can encompass 2×1 configuration to house 2 electrodes or 3×2×3 configuration to house 8 electrodes. The electrode size ranges between 1 cm and 5 cm, and inter-contact gap ranges between 2 mm and 20 mm. For optimal current steering and focusing capabilities, the 3×2×3 configuration is preferred. The overall length of the arrays is 20-50 mm or 50-60 mm or 60-100 mm in order to match the anatomical dimensions of the target. In particular, as the human spinal cord vertebrae is typically 20-30 mm long and the human intervertebral length is about 5-7 mm, electrode array length can be set to 20-60 mm. In addition to the design modularity in configuring the spatial layout, other electrode characteristics can be modified and scaled depending on exact application of interest. The electrode size, inter-electrode gap, material, and adhesive hydrogel resistivity can be personalized for each patient. Larger electrodes may be necessary for persons with thick fat layers due to increased distance between the surface electrodes and targeted neural structures. The hydrogel resistivity can be increased in correlation with the electrode size and gap chosen to avoid cross talk or interference from adjacent stimulating electrodes. Higher resistivity is favored for more homogenous current distribution and can improve the user's comfort level, especially for smaller inter-electrode gaps.

Figure 13:
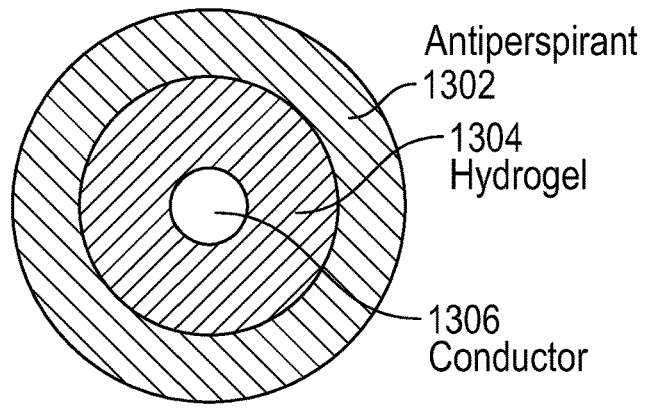
FIG. 13 is an electrode that includes solid antiperspirant regions surrounding a hydrogel region of each electrode pad.

Leakage current between electrode pads in an array reduces the efficacy of neurostimulation and requires higher currents to be applied to the patient, which increases risk. Hydrogel is commonly only placed on the active electrode pads to prevent crosstalk and errant conduction between pads. However, sweat is highly conductive and the presence of sweat underneath the electrode array could cause significant crosstalk. To mitigate the effects of sweat on cross-electrode conduction, an embodiment shown in FIG. 13 may contain solid antiperspirant regions 1302 surrounding the hydrogel region 1304 of each electrode pad. These antiperspirants may consist of metal salts such as aluminum zirconium tricholorohydrex or aluminum chlorate hexahydrate. By placing antiperspirant only around each electrode pad and not on the skin underneath electrodes, crosstalk is reduced without increasing the impedance to the skin. Additional strategies for inhibiting leakage current due to sweat include the use of highly resistive material placed around each electrode and in contact with the skin, the use of resistive microneedles which penetrate the skin and increase lateral resistance between active electrode sites, or the use of an adsorbent material surrounding each electrode that absorbs sweat that would otherwise cause current leakage and crosstalk.

3. Multi-Segmental Targeting of Adjoining and Non-Adjoining Spinal Segments

Figure 14:
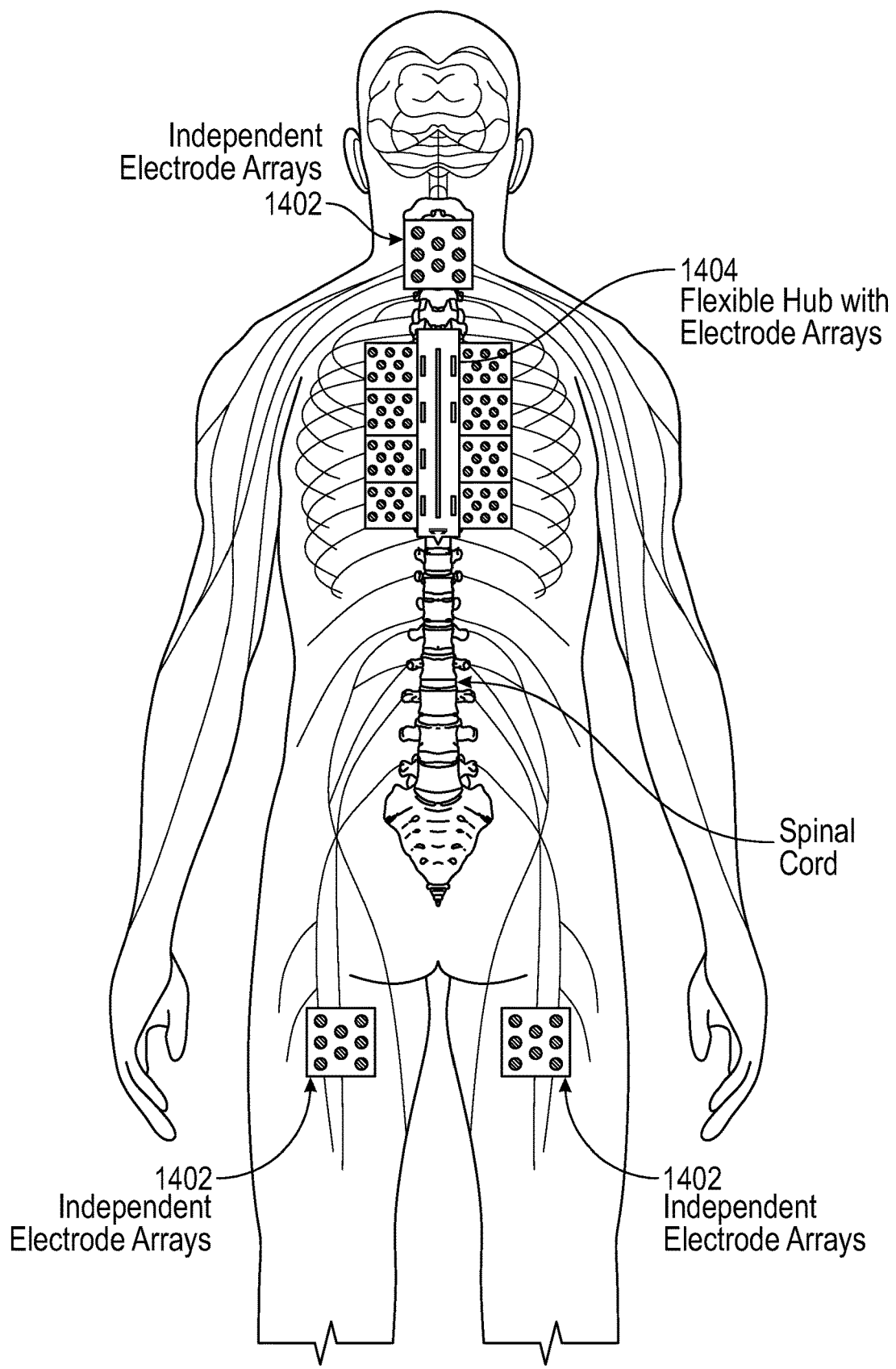
FIG. 14 shows independent electrode arrays, each comprising multiple independent electrodes, and one or more flexible hubs with electrode arrays can be adhered to the user's body to target multiple spinal segments simultaneously or sequentially, or nerves at different locations.

In reference to FIG. 14, independent electrode arrays 1402, each comprising of multiple independent electrodes, and one or more flexible hubs 1404 with electrode arrays can be adhered to the user's body to target multiple spinal segments simultaneously or sequentially, or nerves at different locations. The electrode design provided herein provides superior capabilities over conventional stimulation electrodes because the design 1) eliminates the arduous need of relocating electrodes manually to find the "sweet spot" for optimal stimulation efficacy, 2) allows the automation of the calibration process so that the user does not need to constantly and manually adjust the physical location of the electrode, which is typically routine and tedious when using conventional discrete electrodes, 3) enables simultaneous neuromodulation of multiple adjoining or non-adjoining spinal segments, spinal roots, and nerves, with a plurality of multi-electrode arrays placed at different anatomical locations 1402.

The selective activation of dorsal roots covering specific dermatomes is restricted by the anatomical divergence of dorsal roots as they leave the dorsal ganglia into the spinal cord. While peripheral nerves stemming from each dermatome are bundled together, dorsal root fibers re-arrange into large and small diameter fibers as they approach the spinal cord and transition from spatial bundling into functional bundling, forming a topological organization. Thus, it may be of clinical interest to target neural structures at particular positions. In one example, targeted stimulation at the lumbosacral spinal segments (L2, L3, L4, L5, and S1) and the rootlets around these segments allows for the engagement of lower extremities functions. Though this can be achieved through epidural stimulation as the electrodes are close to the target, non-invasive stimulation using the multi-channel stimulation device in which the stimulation parameters are optimized by considering the sophisticated human body model and by applying the above-stated optimization methods brings the aforementioned benefits over the invasive approach. The proposed electrode array design further provides a flexible stimulation configuration to stimulate multiple targets of interest and enables selective activation of sensory afferents, motor efferents, or dorsal columns, and rostrocaudally for segmental targeting of different spine levels as well as other targeted nerves and internal organs. It is also worthwhile to point out that other non-invasive spinal stimulation approaches or devices, during the past decades till now, do not take the realistic human anatomical model into consideration and stimulation is done by merely placing the stimulation electrodes on the spinous processes and expect that the current simply flow to the desired spinal segments. However, the fact that the shape of vertebral column is irregular, and impact of other biological tissues are not considered lead to the spread of delivered current to multiple segments/biological tissues uncontrollably.

4. Focused Non-Invasive Neuromodulation

Epidural stimulation or other invasive neuromodulation approaches using implantable stimulators can provide a focused stimulation as the electrode is placed close to the target. However, focused stimulation is challenging to achieve through non-invasive method as the electrode is away from the target and multiple non-homogeneous biological tissues exist in between. In particular, during non-invasive spinal neuromodulation, the electrode is adhered to the back of the subject and there exists multiple biological tissues (i.e., skin, fat, muscle, spinal disks, and vertebrae with different dielectric properties) between the electrodes and the target inside the subject while the current also tends to flow through the path having small resistivity based on ohmic law. The majority of delivered electrical current thus travels to not only the closest spinal disk to the underlying spine but also the adjacent ones as they have low resistivity even though this might not be the desired target.

Figure 15:
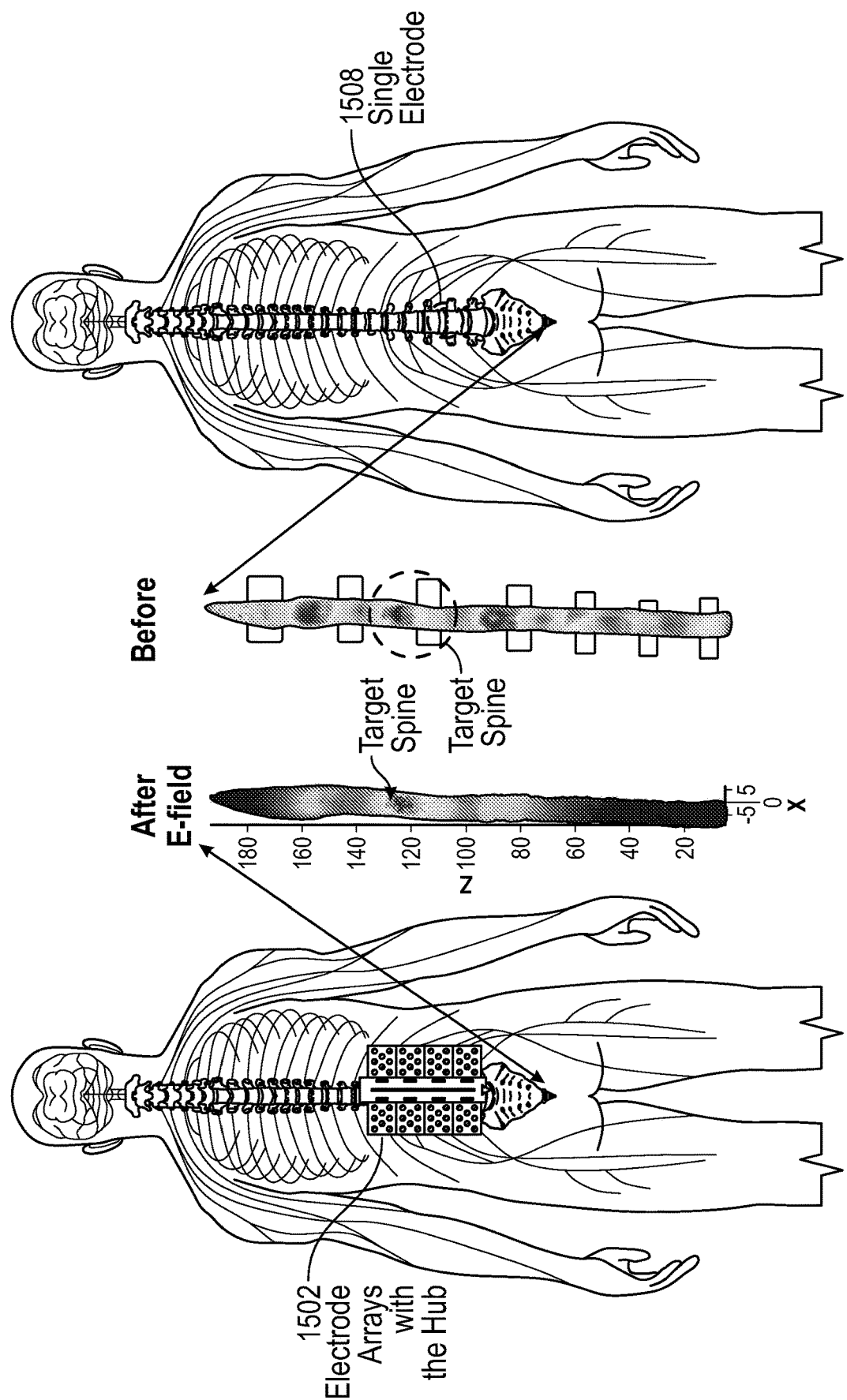
FIGS. 15A-15B illustrate simulations based on 3D realistic human body model.

FIGS. 15A-15B illustrate simulations based on 3D realistic human body model. FIG. 15B shows a conventional approach with a single a non-invasive electrode 1508. FIG. 15A illustrates a system according to the present disclosure that includes multiple electrode arrays 1502 and/or flexible hubs. Referring to FIG. 15A, the hub/electrodes are placed on the subject's back with two return/ground electrodes placed on the celiac crest to deliver electric current to the target spine. The delivered electrical charge is steered to the target by carefully configuring the stimulation parameters at each electrode no matter the electrode is right on top of the target or off the target, providing a better spatial resolution. The stimulation configuration is set through the following steps by 1) identifying the target region (i.e., specific spine segment, nerves, or organs) inside the 3D model; 2) determining the expected electric field strength and current intensity at the target and off the target through the aforementioned optimization methods (e.g., maximum intensity method, linear constrained minimum variance method, and the tSCS optimization method); 3) sending the information to the signal processing device or other computation devices (e.g., laptop, personal computer, DSP, MCU, and FPGA) to estimate and calculate the setting of the stimulation through optimization algorithms; 4) different settings are issued in a pre-arranged order or based on signal recorded from the signal sensors/flexor sensor at certain spatiotemporal order to facilitate specific functions (e.g., upper limbs, lower limbs, or bladder control). The expected electric field strength can be determined by executing a conventional single electrode stimulation simulation (i.e., no optimization performed) and recording the resulting electric field at the target; deliver the stimulation to the practical subject and record the real-world physiological response. This electric field is then used as the expected electric field strength to optimize the stimulation parameters described above. This method and system as shown in FIG. 15A enables a spatial-temporal neuromodulation with optimized focality and selectivity and can be configured based on the topological organization of the target, including the sophisticated spinal cord circuitries. The before and after E-field according to this system and method is shown FIGS. 15A-15B.

5. Multi-Channel Stimulator with Closed-Loop and Open-Loop Control

In order to support the above spatiotemporal neuromodulation with high selectivity and focality, a versatile multiple-channel stimulator capable of adapting the stimulation parameters at each channel independently and precisely is presented in this disclosure.

It is also important to point out that unlike implantable stimulators in which the stimulation current is small (e.g., up to 20 mA), the stimulation current of the non-invasive stimulator or transcutaneous stimulator delivers up to several hundred milliamperes (mA) of current to the human body as the electrode is further away from the neural structures. A common way to implement such a high current driver is through the use of a discrete transformer (e.g., U.S. Pat. No. 5,052,391A). Nonetheless, such transformers are bulky and limit the flexibility and controllability of the stimulation settings to execute non-invasive current steering stimulation. Commercial non-invasive neuromuscular stimulator can only support up to 100 mA stimulation current with limited programmability. Other reported non-invasive transcutaneous spinal stimulators (WO2013071307 A1; US 2019/0022382 A1) only support very primitive function and the output current is often modulated with a high frequency carrier. In particular, the existing non-invasive stimulators possesses a large form factor with low stimulation channel counts. The core of these stimulator is usually a microcontroller or FPGA which is connected to the stimulation driver for configuring the stimulation parameters and the firing timing. With such, extra limitation/constraint on the stimulation versatility is imposed, including 1) an intrinsic delay between each stimulus presents as it takes time for the MCU to execute the stimulation command in a chronological order; 2) larger device form factor required if more MCUs are required to support large number of stimulation channels, 3) the firing timing of each channel cannot be precisely controlled to optimize the stimulating focality.

Figure 16:
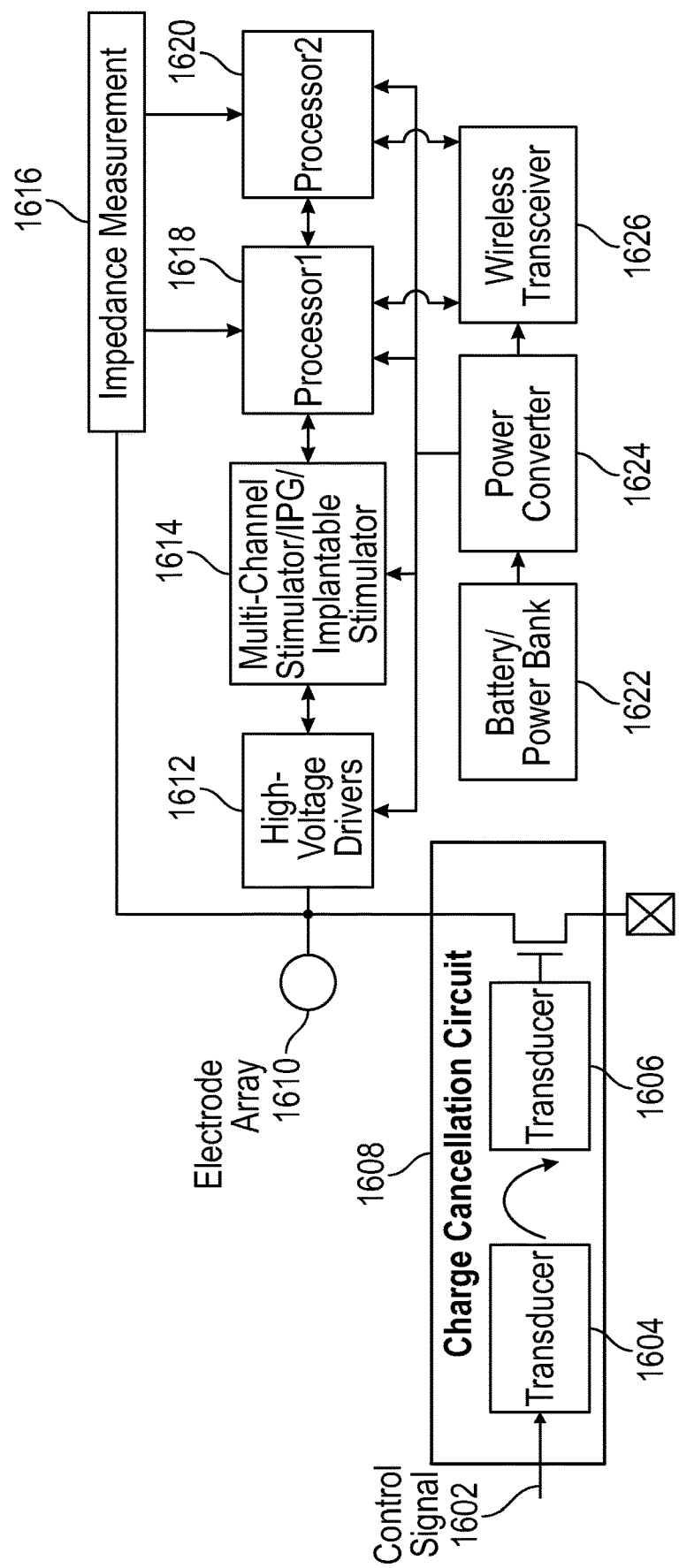
FIG. 16 shows a block diagram of one example of a non-invasive multi-channel stimulator coupled to an electrode array.

FIG. 16 shows a block diagram of one example of a non-invasive multi-channel stimulator coupled to an electrode array 1610. In one embodiment, the core of the non-invasive simulator is a multi-channel implantable stimulator or a stimulator integrated circuit (IC) 1614 with multi-channel voltage or current outputs. In one embodiment, the output of the stimulator is coupled to the high-voltage driver circuitries 1612 for current/voltage amplification. This circuit configuration provides greater advantages over the aforementioned approaches as 1) the current mismatch between each output driver can be minimized as the current source is originated within the same silicon IC; 2) a simple MCU is sufficient to send command to program the stimulator to reduce complexity and support multiple channels; 3) scalability to increase the number of stimulation channels with ease; 4) support concurrent stimulation among all channels when necessary; 5) increase the versatility of stimulation waveforms; 6) decouples the supply voltages of the high-voltage driver from the remaining circuitries to optimize system power consumption; 7) enable the concurrent firing and precise timing control of each stimulation channel to enable focused stimulation. One important feature of this architecture is the ability to support other methods of stimulation with the same electronics architecture. For example, the outputs of the multi-channel stimulator could be coupled to one or more ultrasound transducers to enable ultrasound stimulation, either as a standalone therapeutic or in conjunction with electrical stimulation. By coupling the outputs of the multi-channel stimulator to an array of ultrasound transducers, focused ultrasound stimulation could be achieved that targets deep brain structures, internal organs, or spinal cord segments/spinal nerves. Another potential embodiment involves coupling the outputs of the multi-channel stimulator to one or more LEDs or laser diodes to enable light stimulation or coupled light-electronic stimulation.

In reference to FIG. 16, the power source 1622 (i.e., battery or supercapacitor) is coupled to the power converter 1624. The power converter comprises of multiple power generation circuits, including voltage boost converters, bulk-to-bulk converters, and voltage regulators, to power all the circuits of the non-invasive neuromodulator. The impedance measurement circuit 1616 measures the electrode tissue impedance at each stimulation site in order to 1) continuously asses user-dependent and time-varying physiological changes (e.g., body temperature, sweat electrolytes), 2) safeguard the user from high stimulation output in case of certain detected physical changes (e.g., electrode peeling off the skin), 3) modulate the voltage needed to power the driver circuitries for optimizing system power consumption. If the impedance or stimulation current is lower than a pre-defined value (e.g., 500 ohm and 100 mA), the compliance voltage of the driver circuit can be changed accordingly. However, instead of a simple voltage buffer, the 1st input stage of the impedance measurement circuit is a resistive divider with high input impedance. This can protect the measurement circuit as the voltage on the electrode can easily rise up-to >±20 V when a large current is delivered to the electrodes. One embodiment includes the use of a voltage clamp circuit at the impedance measurement circuit, which limits the electrode overpotential and stimulation current accordingly. Another embodiment may insert a switch (i.e., a MOSFET/BJT switch or multiplexer) between the electrode and the measurement circuit. The switch may not function properly due to high voltage at the electrode interface and the large control voltage required to enable the appropriate on/off transition. The other advantage of certain aspects of the disclosure is that the resistive divider provides an additional discharge path for the residual charge accumulated at the stimulation site (i.e., electrode), in addition to the charge cancellation circuit 1608 that removes the net charge at the electrode at a user-defined timing. The telemetry system comprises a wireless transceiver 1626 such that the user can control the neuromodulator and one or more processors 1618/1620 (e.g., microcontroller, FPGA, CPU, and DSP) wirelessly. In one embodiment, two processors are adopted in the stimulator system. The function of the processors is to 1) translate the received command to the format that the stimulator IC can read and configure the IC and driver to generate the desired stimulation waveform at the desired timing for selective and focused stimulation, 2) analyze and process the received sensors signal from at least one sensor and adapt the stimulation parameters for closed-loop neuromodulation, 3) communicate with the wireless transceiver for full-duplex communication, 4) ensure the safe operation of the system by enabling and disabling each sub-block, 5) contains memory to store the stimulation settings, and 6) scheduling the firing timing of each stimulation channel to ensure the delivered current at any given time does not exceed a safe limit defined by the user. In particular, multiple configurations of stimulation settings can be stored in or be transmitted to the stimulation device in real-time for multitude of defined tasks.

Figure 17:
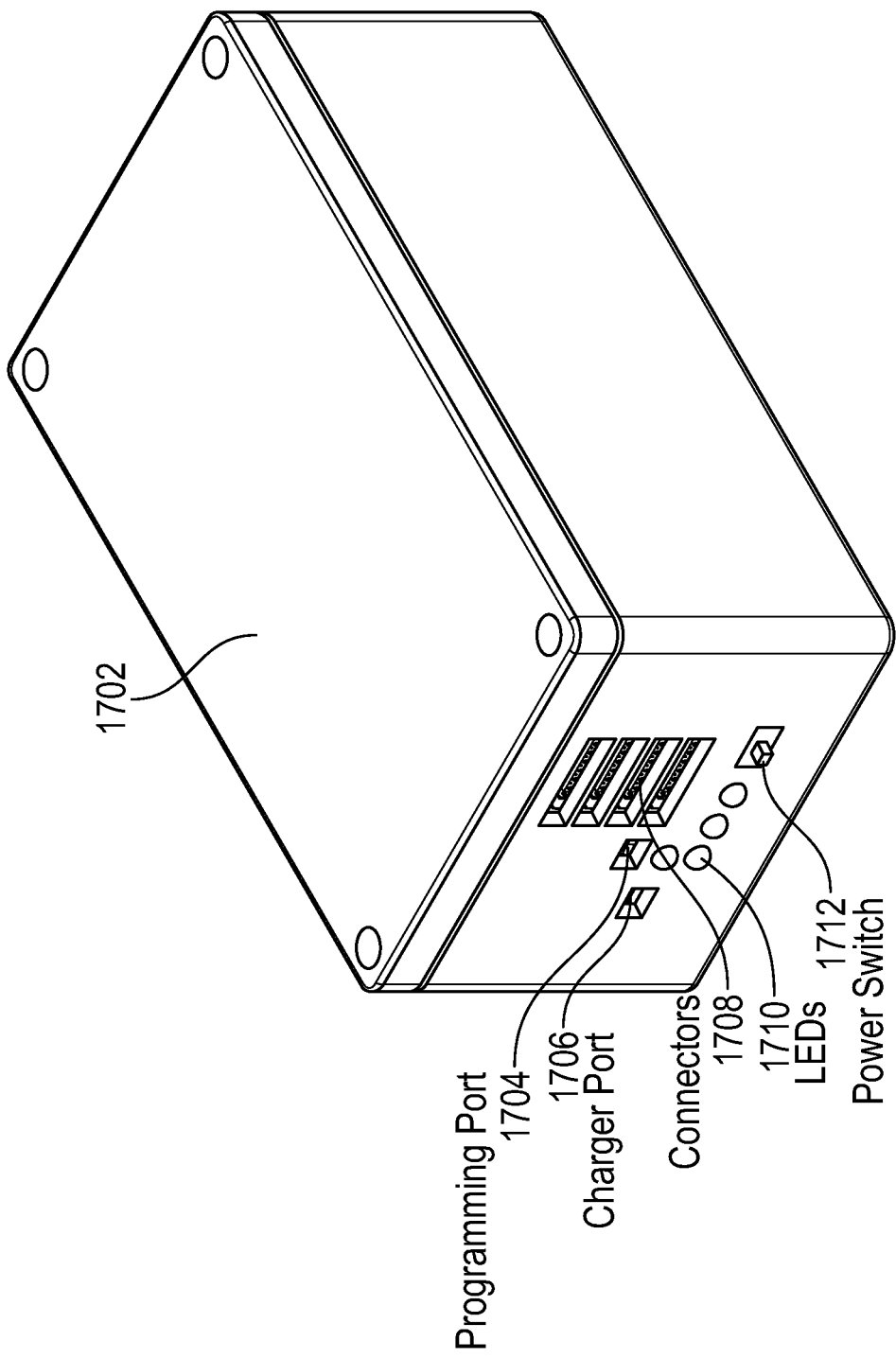
FIG. 17 illustrates one example of a hand-held case that may be used to house an embodiment of a non-invasive stimulator component according to one aspect of the disclosure.

FIG. 17 illustrates one example of a hand-held case 1702 that may be used to house an embodiment of a non-invasive stimulator component according to one aspect of the disclosure. As shown in FIG. 17 a power switch 1712 turns on/off the device. The connectors 1708 connect to the electrode array through the external cables. In addition to delivering electrical stimuli through the connector to the cable, incoming sensory information is also relayed through the cable. At least three light-emitting diodes (LEDs) 1710 are used to indicate the operation status (e.g., wireless connection status and power status) of the non-invasive stimulator. One charger port 1706 (e.g., micro/macro USB port, and USB C) is used for charging and another port 1704 (e.g., micro/macro USB port, USB C, and J-tag) is used to program the processors. Unlike other hand-held devices that often have inconvenient control buttons, the operation of the multichannel stimulator is controlled through a software interface installed on a tablet, cell phone, laptop, or personal computer to wirelessly support a user-friendly interface. This provides a clear advantage in that the detailed status of the system, the configured stimulation parameters, and the recorded feedback signal can be displayed and analyzed in a single device when needed.

The presented multi-channel stimulator possesses scalability. Each stimulator board may contain one stimulator IC and multiple stimulation drivers. Each stimulator board is coupled to another stimulator board through board-to-board connectors. These connectors relay power signal and control signal to control the stimulator boards. In one possible implementation, all the ICs on different boards share the same command line through the board-to-board connectors, reducing the complexity of the system implementation. Although this necessitates a communication protocol so that each stimulator board can recognize its own command format, it also provides a clear advantage that the order of how these boards are stacked is flexible. In another implementation, independent command lines can be coupled to each specific board through board-to-board connectors.

In a preferred embodiment, the stimulator is controlled using a graphical user interface. The interface allows a user to independently select parameters such as amplitude, frequency, pulse width, and stimulation mode for each channel on the stimulator. Profiles with pre-defined stimulation parameters for a specific user or a type of therapy may be saved from the interface or loaded to the interface. In one embodiment, these profiles are saved to a secure cloud storage server and may be loaded into any stimulator by an authorized user. The interface may be used to implement optimization algorithms for focusing the electric field from the array of electrodes on a specific nerve or spinal segment. In a non-limiting example, a physician is presented with a diagram of a patent's spinal nerves superimposed on the patient's body. The physician then selects the spinal segments or spinal nerves they would like to activate and the desired electric field or the $2^{nd}$ derivative of the electric field at the site of activation. The physician may also select avoidance regions where minimizing the magnitude of the electric field during stimulation is desired. Then, the user interface will employ an algorithm to calculate the optimal electrode placement and stimulation parameters for each channel of the stimulator in order to achieve the desired electric field.

Figure 18A:
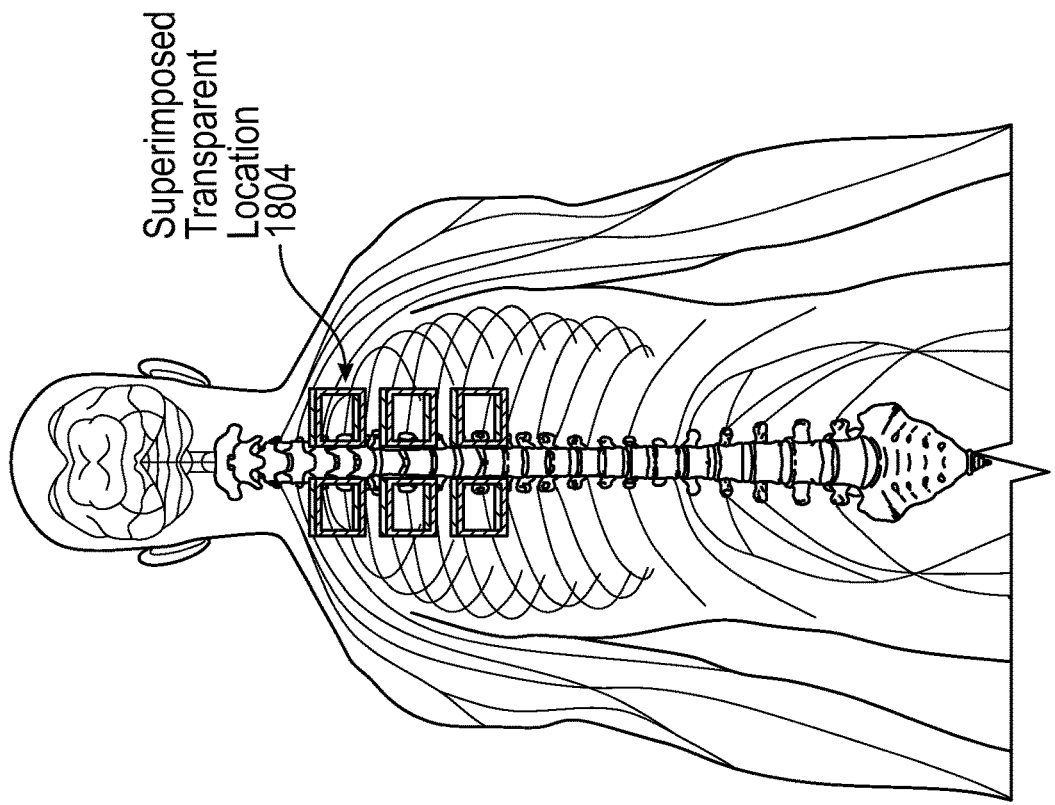
FIGS. 18A-18B show a graphical user interface that may also be used to ensure repeatable and accurate electrode placement using an augmented reality overlay.
Figure 18B:
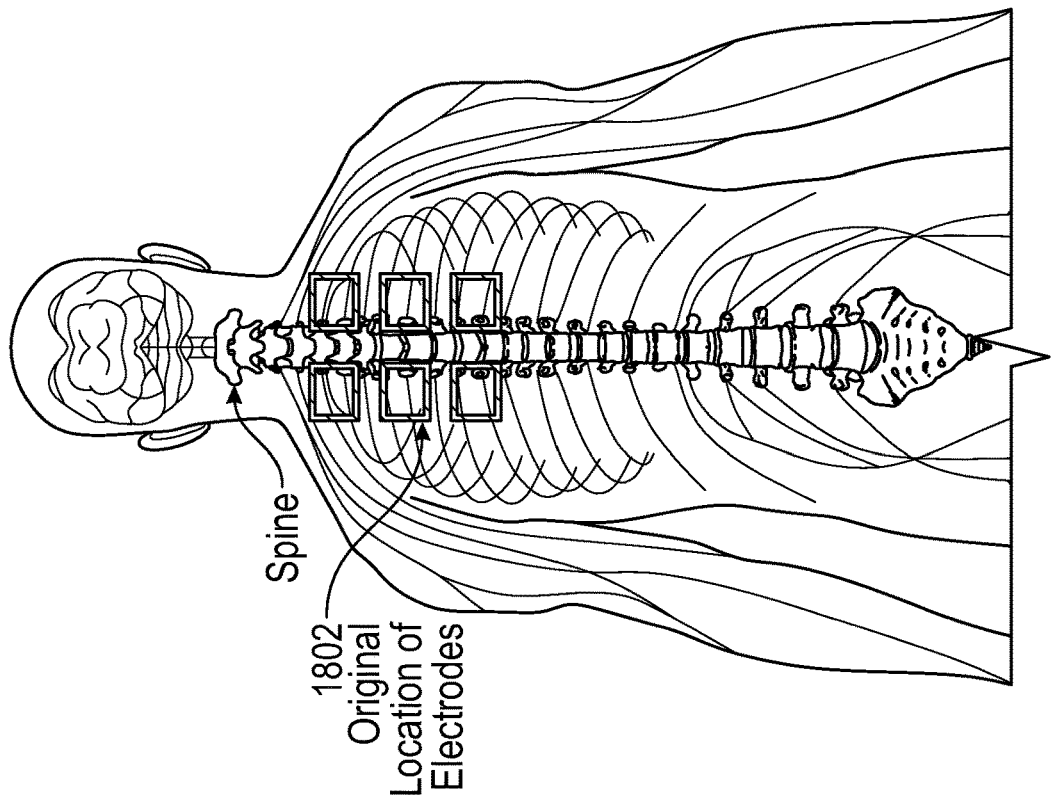

Referring to FIGS. 18A-18B, the graphical user interface may also be used to ensure repeatable and accurate electrode placement using an augmented reality overlay. In one embodiment, the interface is implemented on a tablet computer or mobile device with a built-in camera. When a physician or user places the electrodes on a patient for the first time they may take a picture of the patient with the original electrodes 1802 in place, as shown in FIG. 18A. This image is saved along with the user's stimulation parameters. During subsequent placements, the GUI can display a semitransparent image 1804 of the previous electrode placement superimposed on top of a live image from the camera. This allows the physician or user to confirm that the electrodes are placed consistently. In another embodiment, the interface will display a live feed from a camera of the patient and will use an algorithm to detect the outline and major features of the patient. The algorithm will then calculate the optimal placement of electrodes to stimulate a preselected spinal segment or nerve, and the interface will display the optimal electrode placement site in real-time superimposed over the live image of the patient. This algorithm may be implemented using AI or machine learning techniques.

6. Driver and Discharge Circuits

Referring back to FIG. 16, the charge cancellation circuit 1608 is configured to discharge the net charge accumulated at the electrode and reset the baseline voltage of the output mode. In almost all stimulator designs (i.e., implantable and non-implantable stimulators), the widely adopted approach is to use a MOSFET switch connecting the electrode and the ground, and this switch is activated after stimulation to remove residual electrical charge. However, this approach does not work for the non-invasive stimulator where a large stimulation current is applied. For instance, the discharge switch (e.g., N-type transistor) fails when the electrode voltage and the stimulator output are at a high voltage (e.g., −100V). The gate control signal must be set close to −100V to avoid the undesired turn on of the discharge switch. However, no single transistor can sustain such a gate voltage of >~|30|V. In order to address the above issue, a transducer-like switch is used for the application of residual charge cancellation/removal after stimulation. This is achieved by using a transducer 1604 to convert the original electrical control signal 1602 to other modalities (i.e., light, sound, pressure wave, ultrasound, and force) and then translate it back to electrical signal with another transducer 1606 to activate the switch. In one embodiment, one can convert the electrical control signal to light and use the light to turn on a photodiode, which generates current to activate the discharge switch. More translation steps can be taken but at a cost of signal propagation delay (i.e., the turn-on delay of the switch). Without an appropriate charge cancellation mechanism, the non-invasive stimulator would fail or even damage the tissue under stimulation.

7. Stimulation Modes

Figure 19A:
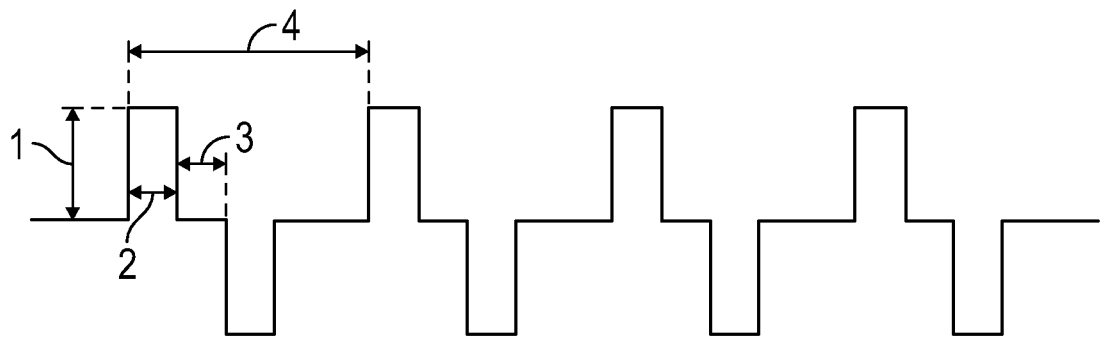
FIGS. 19A-19C show examples of potential basic stimulation waveforms and modes of stimulation, according to the present disclosure.
Figure 19B:
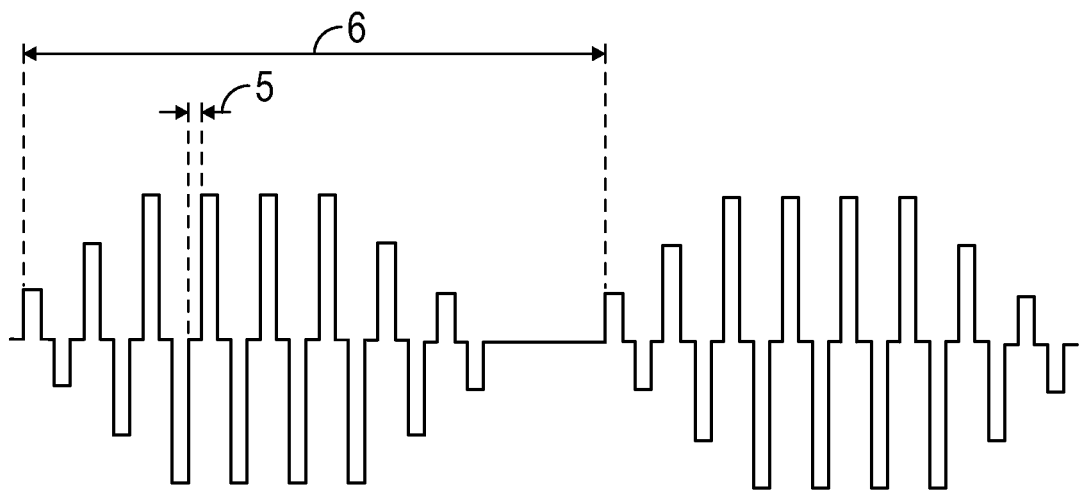
Figure 19C:
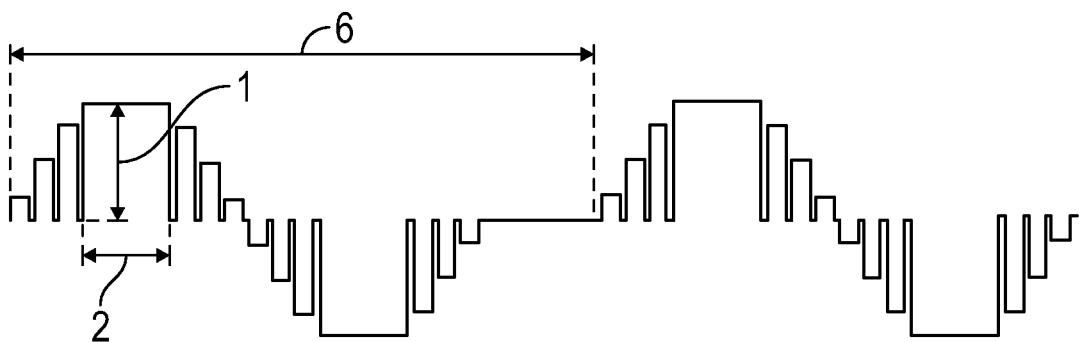

FIGS. 19A-19C show examples of potential basic stimulation waveforms and modes of stimulation, according to the present disclosure. Those of ordinary skill will appreciate a wide array of different stimulation waveforms and modes are enabled by the disclosure and may be adapted based on a number of different patient specific, physiologic or clinical parameters. Common stimulation waveforms, including tonic and burst stimulation, are enabled by the present disclosure. However, the novelties of the disclosure disclosed herein also enable arbitrary and useful waveforms over a wide range of parameters, which may vary in a closed loop method due to input from one or more sensors. By way of explanation and not limitation, three representative output modes will now be described. The three output modes are: single pulse, biphasic ramp, and sinusoidal ramp. A "phase" is used to describe a single cathodic or anodic output whereas a "pulse" is used to describe the matching cathodic and anodic outputs together.

i. Single Pulse Stimulation Mode

FIG. 19A illustrates a single pulse mode configured to deliver a biphasic pulse waveform at a chosen frequency for each channel to fire synchronously or asynchronously. The amplitude 1, phase width 2, interphase delay 3, and frequency 4 can be adjusted. The pulse width ranges 10 μs from 10 ms; the stimulation frequency can be set anywhere between 10 kHz (highest frequency) and any value the user defined (lowest); the stimulation intensity ranges from 0 A to 200 mA per channel with <1 mA resolution. Each electrode channel can have independent values for all parameters and can be activated synchronously and asynchronously. For the application of non-invasive spinal cord stimulation, the stimulation frequency can vary from 5 Hz to 100 Hz. Moreover, for multiple decades, people have tried to use "Russian forms of electrical stimulation", i.e., stimulation frequency at the kilohertz range. In various other aspects, embodiments of the stimulation systems described herein may be adapted and configured for delivery of these types of stimulation parameters and stimulation strategy for non-invasive stimulation.

ii. Biphasic Ramp Stimulation Mode

FIG. 19B illustrates a biphasic ramp mode configured to deliver a sequential, biphasic pulse waveform with increasing and decreasing amplitude. For each pulse, the amplitude, phase width, and interphase delay can be adjusted. For the waveform, the quantity of pulses, inter-pulse delay 5, and overall frequency 6 can be adjusted, as well as the polarity of the leading pulse. Each electrode channel can have independent values for all parameters. This waveform provides the following advantages 1) ramped waveform can reduce the edge effect during stimulation to avoid a large electrical field created at the edge of the electrode to damage/burn the skin, and 2) a sequence of short pulses can deliver the same amount of charge of a long pulse without activating the pain fibers, 3) the 1st few pulses are also used as pre-pulse to lower the threshold of the targeted nerves to enhance the stimulation effectiveness.

iii. Sinusoidal Ramp Stimulation Mode

FIG. 19C illustrates a sinusoidal ramp mode configured to deliver a positive or negative phase that is preceded and followed by narrower phases of the same polarity that increase and decrease in amplitude. This waveform will be followed by a second waveform of opposite polarity. In each stimulation phase, the amplitude 1, phase width 2, and polarity can be adjusted. For the waveform, the quantity of phases, interphase delay, and overall frequency 6 can be adjusted. Each electrode channel can have independent values for all parameters. This feature allows the user to create any pseudo stimulation waveforms, such as triangular or even biomimetic stimulus that can have a stimulation waveform similar to the physiological signals (e.g., EMG, EKG, and neural spikes). Similar to the biphasic ramp mode, this mode provides advantages of 1) ramped waveform to reduce the edge effect during stimulation so that a large electrical field created at the edge of the electrode to damage/burn the skin can be avoided, 2) a group of short pulses can deliver the same amount of charge as a long pulse without activating the nociceptive pain fibers, and 3) the first few pulses are also used as pre-pulses to lower the threshold of the targeted nerves to enhance the stimulation effectiveness.

8. Calibration Modes

Figure 20A:
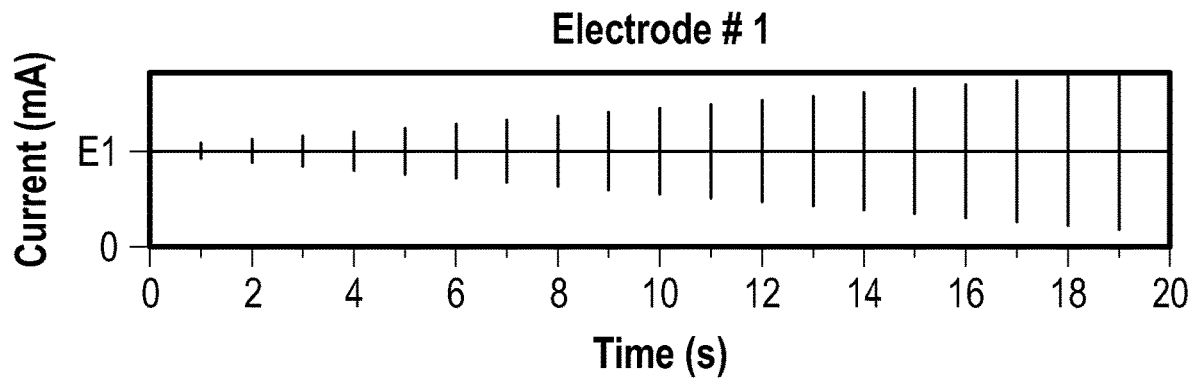
FIGS. 20A-20E illustrate various calibration protocols according to the present disclosure.
Figure 20B:
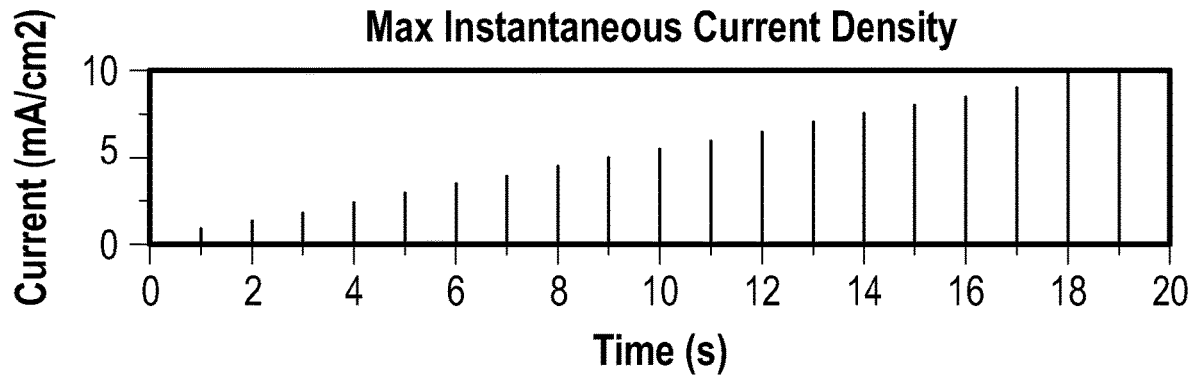
Figure 20C:
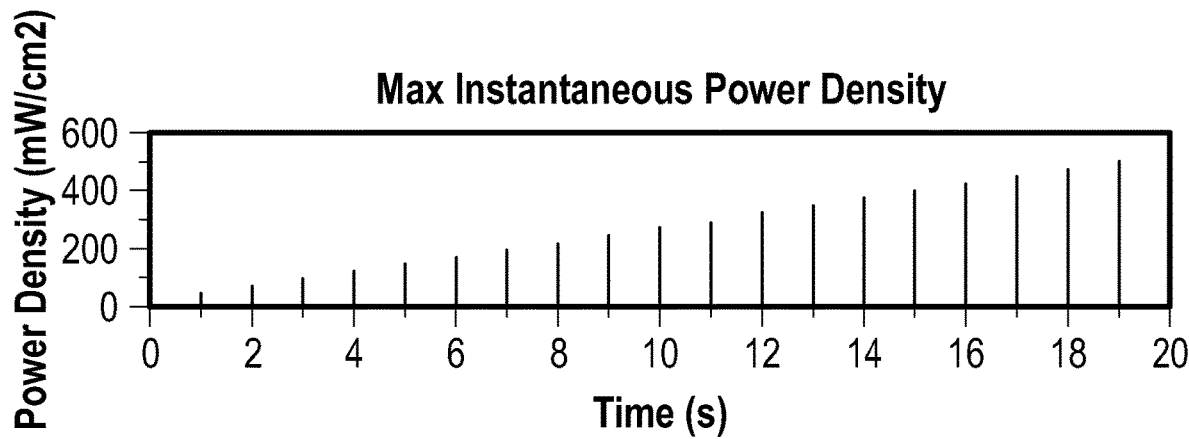
Figure 20D:
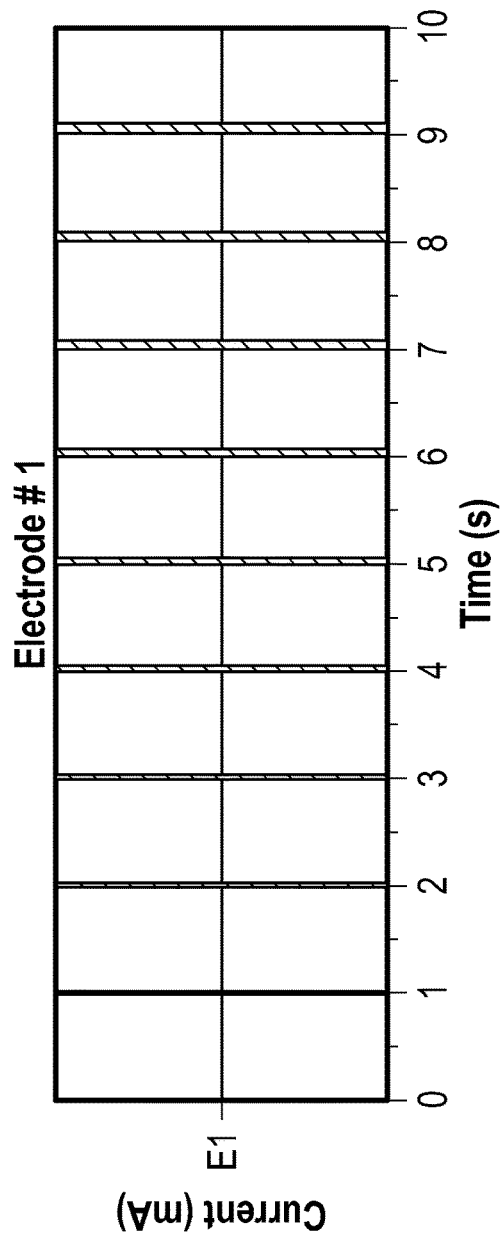
Figure 20E:
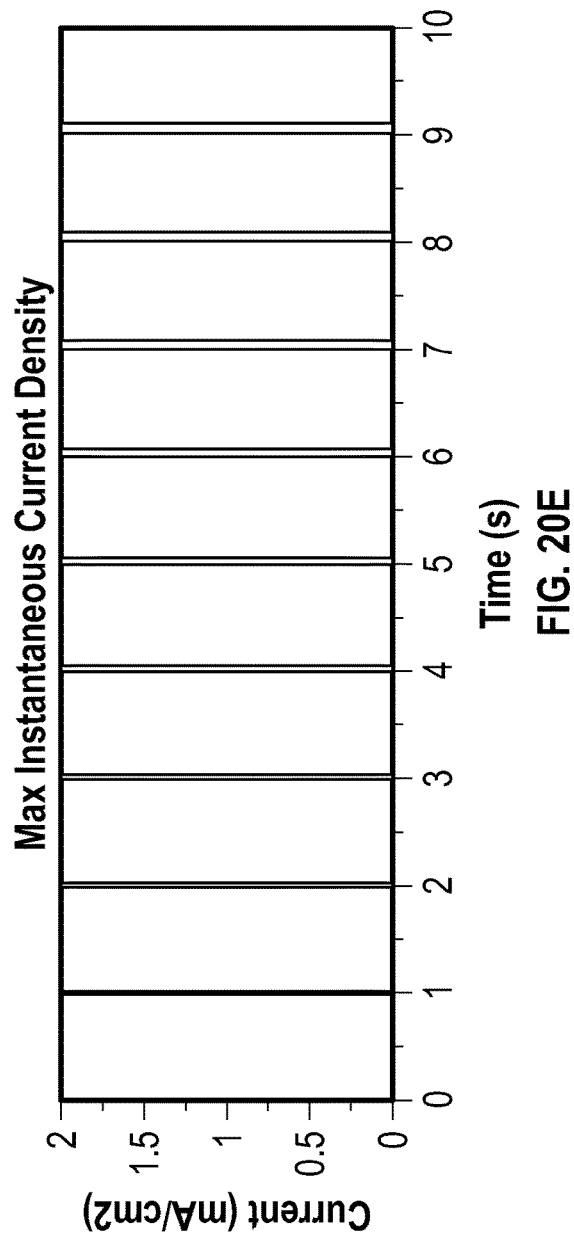

Devices of the present disclosure are configured to support at least two calibration protocols. In reference to FIGS. 20A-20E, a first protocol as shown in FIGS. 20A-20C delivers incremental ramp up of current intensity in order to classify the minimum current densities required to reach the targeted neural fibers perception, sensory, and motor activation thresholds. Once the motor thresholds are classified, the anatomical location of the electrodes and relevant distance from the spinal cord can be detected by registering PRM reflexes, EMG amplitudes, and latencies. Asymmetrically and transversely aligned electrodes (either left or right) can be stimulated to activate dorsal roots and the consequential myotome. Since the first protocol classifies the minimum current fields and densities required to activate the targeted neural fibers but provides limited insights into the role of frequency and temporal summation, additional aspects include a second novel temporal ramp-up calibration protocol as shown in FIGS. 20D-20E to detect the influence of varying frequency on activation thresholds (FIGS. 20D-20E).

In the case of transcutaneous spinal cord stimulation, the influence of frequency is particularly important because dorsal afferents are more susceptible to varying the rate of polarity transitions than pulse width. This is explained by the lack of correlation between PRM reflex latency and various pulse widths, especially when aligning EMG peaks with the time stamps of polarity transitions. Thus, a temporal calibration procedure has significant implications in expanding the range of insights gained during the calibration phase and possible interventional stimulation parameters that best suit different patient demographics. Specifically, the influence of temporal summation on the sensory afferents thresholds, as well as the synaptic mechanisms of the spinal neural circuits in projecting into the ventral motor efferents and subsequent innervated myotomes, can be better understood. Practical implementation could involve decreasing frequency in set pulses from the maximum allowable by the stimulation hardware until the subject's perception threshold is reached or the subject experiences paresthesia. Logarithmic sweeping of frequency can be used to reduce the total number of steps, saving time and power.

9. Special Safety Controls

Figure 21A:
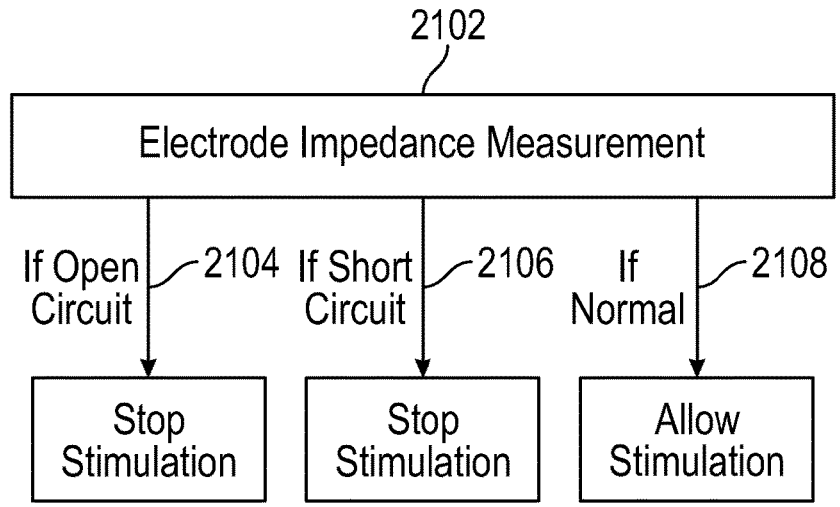
FIGS. 21A-21B demonstrate a flow chart and timing diagram, respectively, of an impedance measurement procedure.
Figure 21B:
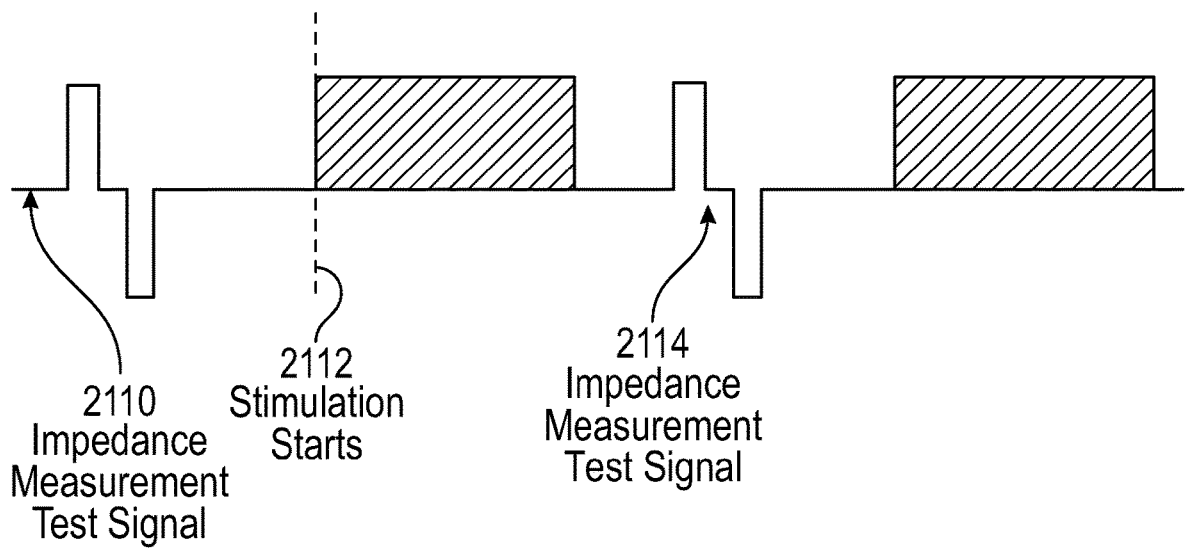

FIGS. 21A-21B demonstrate a flow chart and timing diagram, respectively, of an impedance measurement procedure. Referring to FIGS. 21A-21B, while measuring the impedance (step 2102 of FIG. 21A), a non-invasive stimulator can deliver an impedance measurement test signal 2110 comprising a small current (i.e., 1 µA to 5 mA at a pulse width of from 10 µs to 2 ms) to the electrode and this voltage can be sensed by electrode impedance measurement circuits. If the measured impedance exceeds a pre-set maximum (e.g., 1.5, 3, or 5 kOhm), the system can determine that an open circuit is present (step 2104 of FIG. 21A) in which either the electrode is not correctly connected to stimulator or the electrode has deteriorated. If the measured impedance is less than the pre-set minimum (e.g., 50 Ohm), as the system can determine that a short circuit is present (step 2106 of FIG. 21A) in which two or more electrodes may have physical and electrical contact with another. If the measured impedance is within the pre-set upper and lower bound, the system can determine that the stimulator is ready to perform stimulation (step 2108 of FIG. 21A). Moreover, in addition to measuring the impedance only before the stimulation onset, impedance of each electrode can be measured during stimulation. In one embodiment, as shown in the time diagram of FIG. 21B, impedance can be measured on-the-fly (impedance measurement 2114) between each group of stimuli 2112 to ensure the continuing safety of the stimulation.

Figure 22:
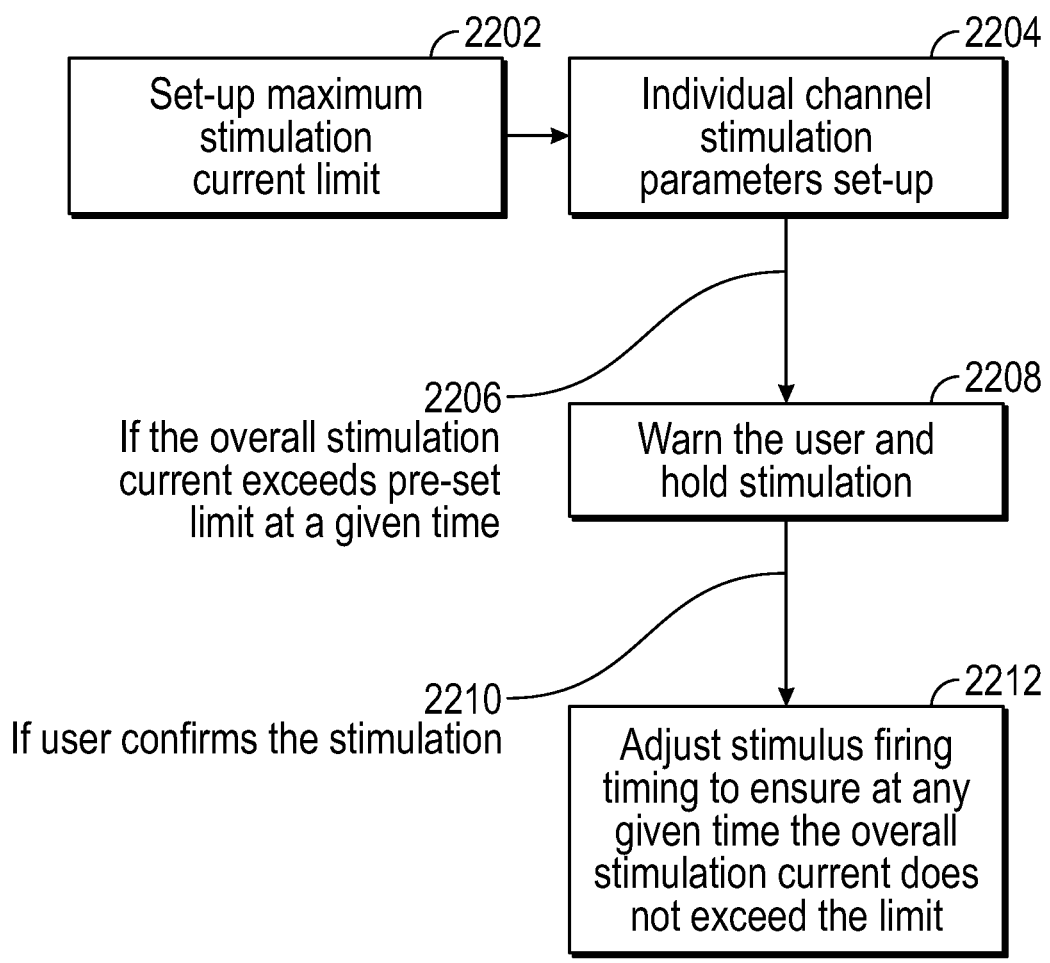
FIG. 22 shows another safety feature and operation flow of the stimulator.

FIG. 22 shows another safety feature and operation flow of the stimulator. In order to protect the subject receiving electrical stimulation, the user or system can set a maximal output current 2202 to ensure the overall current delivered through the skin to the subject does not exceed that limit. Subsequently, stimulation parameters for each individual channel 2204 can be configured and once the overall current exceeds the pre-set limit 2206, the programmer can warn the user to revise the parameters 2208. However, in some circumstances, even if the configured overall stimulation exceeds the pre-set safe limit, the device can interleave the onset of stimuli from each channel to ensure that at any given time point, the overall stimulation would not exceed the preset safe value 2212. The scheduling is achieved through the algorithms embedded in the signal processing device or external control device of the system. The algorithm takes in the user-defined parameters, including but not limited to pulse width, amplitude, and frequency, of the waveform of a set of channels. In one embodiment, the algorithm would construct a firing sequence such that in any given time, the combination of the amplitude of each channel will not exceed a limit, which can be defined by the user, while the root-mean-square difference of frequency between the users-defined parameter and the fired parameter is minimized. The calculation process involves intensively randomly generating and trialing different possible combinations of channels to search and optimize the answer. The key for the answer being able to perfectly interleave all amplitude peaks with each other to avoid exceeding the limitation for indefinitely long of time is the property of the remainder.

In existing implants or non-invasive stimulators, due to the fact that the type of electrode is mostly fixed, the influence of the electrode size is not incorporated into the stimulation parameter setting. However, there is a safety limit for the power per $cm^2$ of the electrode delivered to the skin, based on the Food and Drug Administration's (FDA) regulation and any configured stimulation parameters cannot exceed this limit. In some aspects of embodiments of the inventive system, after the electrode size is selected and the stimulation parameters are configured, the average delivered power density per $cm^2$ is calculated and the derived power density is compared to the preset safety limit (e.g., 0.25 $W/cm^2$, the FDA limit for electrical muscular stimulation). Moreover, different types of electrodes have their own maximal safe deliverable charge density ($C/cm^2$). This method can also be used to examine the delivered charge density. Once the delivered charge or power density exceeds the pre-set stimulation safety limit, the stimulation would stop and the user would be warned to revise the stimulation parameters or use electrodes with different size.

10. Methods and Applications

A. Selective Spatiotemporal Spinal Neuromodulation to Enable Upper Limb Functions It has been shown that conventional tonic spinal stimulation on C5 vertebra can facilitate the voluntary hand function of the paralyzed subject. However, the treatment efficacy is not optimized as the injected electrical current spreads to other off targets and this tonic stimulation interrupts the pathway of afferent sensory signal transmission.

In particular, common upper limb functions include hand grip, wrist extension, finger extension, elbow bending, shoulder abduction, and pronating/supinating the arm, governed by nerves originating from C5-T1 spines. By using the disclosed non-invasive neuromodulation device and the focused and selective stimulation method, hand grip, wrist extension, and finger flexion can be facilitated by selectively stimulating C8-T1 spinal segments or spinal roots entering these segments non-invasively. Lower arm function can be facilitated by selectively stimulating C7, and C8 spines and spinal roots entering these segments; upper arm motor functions can be facilitated by selectively stimulating C6 and C6-C8 spines and spinal roots entering these segments; shoulder motor function can be facilitated by selectively stimulating C5-C6 and C5-C8 spines or spinal roots entering these segments. By incorporating the data recorded by signal sensors worn by the subject, stimulation paradigms to stimulate different targets are altered in real-time based on the posture of the subject, providing a spatiotemporal non-invasive neuromodulation with high selectivity and focality. This also avoids the drawback of conventional tonic transcutaneous spinal stimulation adopted by others. Selective stimulation on the right or left spinal nerves can be used for SCI, stroke, MS, and Parkinson, and essential tremor.

B. Selective Spatiotemporal Spinal Neuromodulation to Enable Back Posture Control Back posture is regulated by muscles receiving command from the spinal cord. The human back muscles consist of three layers of muscles: deep, superficial and intermediate layers. The intermediate layer contains the three paraspinal muscles (i.e., Iliocostalis, Longissimus, and Spinalis) that control the functioning of back. Common back functions include leaning side to side, leaning forwards to backwards, twisting, tilting neck left and right, and maintaining posture. By using the disclosed spatiotemporal non-invasive neuromodulation device and method to perform non-tonic stimulation, the above back function can be facilitated. In particular, tilting the neck posture can be facilitated by selectively stimulating T1-T5 and C2-C6 spinal segments and the spinal roots entering these segments; leaning side to side can be facilitated by selectively stimulating C2-C6 and T1-T5 spinal segments and the spinal roots entering these segments; leaning forwards and backwards can be facilitated by selectively modulating C2 and T1-T12 spinal segments and the spinal roots entering these segments; twisting be facilitated by selectively stimulating C4-C6 and T1-T12 spinal segments and the spinal roots entering these segments; maintaining posture can be facilitated by modulating the network residing in C1-T12 spinal segments. By incorporating the data recorded by a flex sensor worn by the subject, stimulation paradigms to stimulate different targets are altered in real-time based on the posture of the subject, providing a spatiotemporal non-invasive neuromodulation with high selectivity and focality as well as closed-loop control.

C. Selective Spatiotemporal Spinal Neuromodulation to Improve Bladder Control

The muscles used in micturition are innervated by the nerves in sacral plexus and lumbar plexus. Pelvic nerve that originates from S2, S3, and S4 spine excite the bladder and relax the urethra to empty the urinary bladder, control opening and closing of the internal urethral sphincter. Pudental nerves also arises from S2, S3, and S4 spine to provide sensory feedback. It innervates the external anal sphincter and the external urethral sphincter in both males and females. On other hand, lumbar sympathetic nerves arise from the L2-L3 and innervate the bladder body and excite the bladder base and urethra. Tonic stimulation has also been used restore bladder control by stimulating T11 and L1 vertebra (i.e., L2 and S1 spine) while the above three nerves governing the bladder function might be activated concurrently. This might impact the effectiveness of the treatment as Pelvic Splanchnic nerves and lumbar sympathetic nerves serve opposite function on bladder control and conventional non-invasive spinal cord stimulation would activate these nerves together due to its lack of focality and selectivity. A better bladder function control can be facilitated using the disclosed neuromodulation device and method to selectively stimulation S2-S4 spine for bladder emptying sensing and L2-L3 for improve urine storage.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A transcutaneous electrical stimulation system, comprising:
   a plurality of electrodes configured to be in contact with a skin surface of a patient;
   a flexible hub electrically connected to the electrodes and configured to be in contact with the patient;
   a bend sensor disposed in the hub and configured to measure a curvature of the hub;
   a signal processing device electrically coupled to the plurality of electrodes and the bend sensor, the signal processing device being configured to change stimulation settings of the plurality of electrodes based on the curvature of the hub, wherein a curvature signal from the hub is used to dynamically restrict stimulation intensity to sub-motor threshold levels; and
   a multi-channel stimulator comprising at least one stimulation channel for each of the plurality of electrodes, the multi-channel stimulator being configured to receive the changed stimulation settings from the signal processing device and deliver electrical stimulation at each stimulation channel through its corresponding electrode.

2. The system of claim 1, wherein the bend sensor is composed of one or more accelerometers, gyroscopes, magnetometers, inertial measurement units, or some combination thereof.

3. The system of claim 2, wherein the bend sensor is also configured to measure posture or movement.

4. The system of claim 1, further comprising electrical connectors detachably connecting the electrodes, hub, and electronics.

5. The system of claim 1, wherein electrodes are arranged in both a longitudinal direction and a transverse direction relative to the spinal cord and ganglion roots in an array configuration.

6. The system of claim 1, wherein two or more electrodes are configured to selectively stimulate biological targets.

7. The system of claim 6, wherein a stimulation target of the biological targets is the spinal cord, spinal ganglion roots, sympathetic and parasympathetic nerves, peripheral nerves, or visceral organs.

8. The system of claim 6, wherein a stimulation target of the biological targets is a specific spinal column and specific nerves or roots originating or being innervated by the selected spinal column.

9. The system of claim 6, wherein the multi-channel stimulation is configured to enhance and focalize the electrical field or the tangential electrical field, or the derivative of an electrical field or a tangential electrical field at the selected target or targets and minimize the electrical field, the tangential electric field, or the derivative of the electrical field in other locations.

10. The system of claim 1, further comprising sensors for electromyography, skin temperature, heart rate, blood oxygenation, blood pressure, sweat concentration, muscle hemodynamics, or a combination thereof.

11. The system of claim 10, wherein the electromyography sensor is configured to detect sub-motor muscle activation during stimulation for the purposes of reducing skin irritation or is configured to detect reflex signals at selected muscles.

12. The system of claim 1, further comprising one or more ultrasounds transducers connected to the outputs of the multi-channel stimulator and configured to deliver ultrasound stimulation to patient.

13. The system of claim 1, wherein the multi-channel stimulator is non-invasive and a core of the non-invasive multi-channel stimulator is a multi-channel implantable stimulator or a stimulator integrated circuit (IC).

14. A method of providing transcutaneous electrical stimulation to modulate the nervous system of a subject, the method comprising:
   placing one or more electrodes in contact with a skin surface of a subject above a stimulation area;
   attaching the electrodes to a flexible hub containing sensors disposed in the flexible hub for measuring curvature of the hub;
   specifying the stimulation targets, estimating or calculating a stimulation configuration for each channel to perform focused stimulation based on the curvature of the hub, wherein a curvature signal from the hub is used to dynamically restrict stimulation intensity to sub-motor threshold levels;
   providing a first electrical stimulation therapy through at least some of the electrodes to perform selective stimulation;
   measuring the curvature of the flexible hub and physiological sensors; and
   providing a second stimulation therapy through at least some of the electrodes, a difference between the first stimulation therapy and the second stimulation therapy being based on a measured change in the hub's curvature and sensors readout.

15. The method of claim 14, wherein the neuromodulation is employed to target a neural network incorporating multiple segments and specific targets concurrently or sequentially or randomly.

16. The method of claim 14, further including the following steps:
   placing one or more electrodes and one or more sensors on the subject's skin; stimulating the subject's skin with the one or more electrodes during a first stimulation; measuring an output of the electrodes during a first stimulation with the one or more sensors;
   adjusting at least one stimulation parameter of the one or more electrodes based on the measured output; and
   stimulating the subject's skin with the one or more electrodes during a second stimulation.

* * * * *